(12) United States Patent
Cohen et al.

(10) Patent No.: US 12,390,330 B2
(45) Date of Patent: Aug. 19, 2025

(54) FORCE LIMITING MECHANISM FOR PROSTHETIC HEART VALVE DELIVERY APPARATUS

(71) Applicant: Edwards Lifesciences Corporation, Irvine, CA (US)

(72) Inventors: Oren Cohen, Kadima (IL); Elazar Levi Schwarcz, Netanya (IL); Eitan Atias, Tel Aviv (IL); Tomer Saar, Pardes Hanna-Karkur (IL)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 818 days.

(21) Appl. No.: 17/553,688

(22) Filed: Dec. 16, 2021

(65) Prior Publication Data

US 2022/0104944 A1    Apr. 7, 2022

Related U.S. Application Data

(63) Continuation of application No. PCT/US2020/040323, filed on Jun. 30, 2020.
(Continued)

(51) Int. Cl.
*A61F 2/24* (2006.01)
*A61F 2/95* (2013.01)

(52) U.S. Cl.
CPC .......... *A61F 2/2439* (2013.01); *A61F 2/2418* (2013.01); *A61F 2/243* (2013.01); *A61F 2/2436* (2013.01); *A61F 2/9517* (2020.05)

(58) Field of Classification Search
CPC ...... A61F 2/2439; A61F 2/2418; A61F 2/243; A61F 2/2436; A61F 2/9517; A61F 2/962
See application file for complete search history.

(56) References Cited

U.S. PATENT DOCUMENTS

| 3,409,013 | A | 11/1968 | Berry |
| 3,548,417 | A | 12/1970 | Kisher |

(Continued)

FOREIGN PATENT DOCUMENTS

| DE | 0144167 C | 9/1903 |
| DE | 2246526 A1 | 3/1973 |

(Continued)

OTHER PUBLICATIONS

H.R. Andersen, et al. "Transluminal Implantation of Artificial Heart Valve. Description of a New Expandable Aortic alve and Initial Results with implantation by Catheter Technique in Closed Chest Pig," European Heart Journal, No. 3. pp. 704-708. 1992.

(Continued)

*Primary Examiner* — Sarah W Aleman
(74) *Attorney, Agent, or Firm* — Klarquist Sparkman, LLP; Joel B. German

(57) ABSTRACT

A medical assembly can include a radially expandable prosthetic heart valve and a delivery apparatus. The delivery apparatus can include a handle, an actuation member, and a force limiting mechanism within the handle including a pivot arm coupled to a base portion. The actuation member can apply a proximally directed force to the prosthetic valve to cause the valve to expand. The actuation member can be coupled to the pivot arm such that a force applied to the actuation member causes the pivot arm to pivot. The force limiting mechanism can pinch the actuation member between the pivot arm and the base portion when the force applied to the actuation member exceeds a predetermined force to prevent proximal movement of the actuation member and can allow proximal movement of the actuation member to produce radial expansion of the prosthetic valve when the force applied is less than the predetermined force.

20 Claims, 9 Drawing Sheets

Related U.S. Application Data

(60) Provisional application No. 62/870,372, filed on Jul. 3, 2019.

(56) References Cited

U.S. PATENT DOCUMENTS

| | | | |
|---|---|---|---|
| 3,587,115 A | 6/1971 | Shiley | |
| 3,657,744 A | 4/1972 | Ersek | |
| 3,671,979 A | 6/1972 | Moulopoulos | |
| 3,714,671 A | 2/1973 | Edwards et al. | |
| 3,755,823 A | 9/1973 | Hancock | |
| 4,035,849 A | 7/1977 | Angell et al. | |
| 4,056,854 A | 11/1977 | Boretos et al. | |
| 4,106,129 A | 8/1978 | Carpentier et al. | |
| 4,222,126 A | 9/1980 | Boretos et al. | |
| 4,265,694 A | 5/1981 | Boretos et al. | |
| 4,297,749 A | 11/1981 | Davis et al. | |
| 4,339,831 A | 7/1982 | Johnson | |
| 4,343,048 A | 8/1982 | Ross et al. | |
| 4,345,340 A | 8/1982 | Rosen | |
| 4,373,216 A | 2/1983 | Klawitter | |
| 4,406,022 A | 9/1983 | Roy | |
| 4,441,216 A | 4/1984 | Ionescu et al. | |
| 4,470,157 A | 9/1984 | Love | |
| 4,535,483 A | 8/1985 | Klawitter et al. | |
| 4,574,803 A | 3/1986 | Storz | |
| 4,592,340 A | 6/1986 | Boyles | |
| 4,605,407 A | 8/1986 | Black et al. | |
| 4,612,011 A | 9/1986 | Kautzky | |
| 4,643,732 A | 2/1987 | Pietsch et al. | |
| 4,655,771 A | 4/1987 | Wallsten | |
| 4,692,164 A | 9/1987 | Dzemeshkevich et al. | |
| 4,733,665 A | 3/1988 | Palmaz | |
| 4,759,758 A | 7/1988 | Gabbay | |
| 4,762,128 A | 8/1988 | Rosenbluth | |
| 4,777,951 A | 10/1988 | Cribier et al. | |
| 4,787,899 A | 11/1988 | Lazarus | |
| 4,787,901 A | 11/1988 | Baykut | |
| 4,796,629 A | 1/1989 | Grayzel | |
| 4,820,299 A | 4/1989 | Philippe et al. | |
| 4,829,990 A | 5/1989 | Thuroff et al. | |
| 4,851,001 A | 7/1989 | Taheri | |
| 4,856,516 A | 8/1989 | Hillstead | |
| 4,878,495 A | 11/1989 | Grayzel | |
| 4,878,906 A | 11/1989 | Lindemann et al. | |
| 4,883,458 A | 11/1989 | Shiber | |
| 4,922,905 A | 5/1990 | Strecker | |
| 4,966,604 A | 10/1990 | Reiss | |
| 4,979,939 A | 12/1990 | Shiber | |
| 4,986,830 A | 1/1991 | Owens et al. | |
| 4,994,077 A | 2/1991 | Dobben | |
| 5,007,896 A | 4/1991 | Shiber | |
| 5,026,366 A | 6/1991 | Leckrone | |
| 5,032,128 A | 7/1991 | Alonso | |
| 5,037,434 A | 8/1991 | Lane | |
| 5,047,041 A | 9/1991 | Samuels | |
| 5,059,177 A | 10/1991 | Towne et al. | |
| 5,080,668 A | 1/1992 | Bolz et al. | |
| 5,085,635 A | 2/1992 | Cragg | |
| 5,089,015 A | 2/1992 | Ross | |
| 5,152,771 A | 10/1992 | Sabbaghian et al. | |
| 5,163,953 A | 11/1992 | Vince | |
| 5,167,628 A | 12/1992 | Boyles | |
| 5,192,297 A | 3/1993 | Hull | |
| 5,266,073 A | 11/1993 | Wall | |
| 5,282,847 A | 2/1994 | Trescony et al. | |
| 5,295,958 A | 3/1994 | Shturman | |
| 5,332,402 A | 7/1994 | Teitelbaum | |
| 5,360,444 A | 11/1994 | Kusuhara | |
| 5,370,685 A | 12/1994 | Stevens | |
| 5,397,351 A | 3/1995 | Pavcnik et al. | |
| 5,411,055 A | 5/1995 | Kane | |
| 5,411,552 A | 5/1995 | Andersen et al. | |
| 5,443,446 A | 8/1995 | Shturman | |
| 5,480,424 A | 1/1996 | Cox | |
| 5,500,014 A | 3/1996 | Quijano et al. | |
| 5,545,209 A | 8/1996 | Roberts et al. | |
| 5,545,214 A | 8/1996 | Stevens | |
| 5,549,665 A | 8/1996 | Vesely et al. | |
| 5,554,185 A | 9/1996 | Block et al. | |
| 5,558,644 A | 9/1996 | Boyd et al. | |
| 5,571,175 A | 11/1996 | Vanney et al. | |
| 5,584,803 A | 12/1996 | Stevens et al. | |
| 5,591,185 A | 1/1997 | Kilmer et al. | |
| 5,591,195 A | 1/1997 | Taheri et al. | |
| 5,607,464 A | 3/1997 | Trescony et al. | |
| 5,609,626 A | 3/1997 | Quijano et al. | |
| 5,628,792 A | 5/1997 | Lentell | |
| 5,639,274 A | 6/1997 | Fischell et al. | |
| 5,665,115 A | 9/1997 | Cragg | |
| 5,716,417 A | 2/1998 | Girard et al. | |
| 5,728,068 A | 3/1998 | Leone et al. | |
| 5,749,890 A | 5/1998 | Shaknovich | |
| 5,756,476 A | 5/1998 | Epstein et al. | |
| 5,769,812 A | 6/1998 | Stevens et al. | |
| 5,800,508 A | 9/1998 | Goicoechea et al. | |
| 2011/0077621 A1 | 3/2011 | Graham et al. | |
| 2014/0296962 A1* | 10/2014 | Cartledge | A61F 2/95 623/1.11 |
| 2017/0065406 A1* | 3/2017 | Calomeni | A61F 2/2436 |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0850607 A1 | 7/1998 |
| EP | 1057460 A1 | 12/2000 |
| EP | 1088529 A2 | 4/2001 |
| EP | 1570809 A1 | 9/2005 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9829057 A1 | 7/1998 |
| WO | 9930646 A1 | 6/1999 |
| WO | 9933414 A1 | 7/1999 |
| WO | 9940964 A1 | 8/1999 |
| WO | 9947075 A1 | 9/1999 |
| WO | 0018333 A1 | 4/2000 |
| WO | 0041652 A1 | 7/2000 |
| WO | 0135878 A2 | 5/2001 |
| WO | 0149213 A2 | 7/2001 |
| WO | 0154624 A1 | 8/2001 |
| WO | 0154625 A1 | 8/2001 |
| WO | 0162189 A1 | 8/2001 |
| WO | 0047139 A9 | 9/2001 |
| WO | 0164137 A1 | 9/2001 |
| WO | 0176510 A2 | 10/2001 |
| WO | 0222054 | 3/2002 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 0249540 A2 | 6/2002 |
| WO | 03047468 | 6/2003 |
| WO | 2005034812 A1 | 4/2005 |
| WO | 2005055883 A1 | 6/2005 |
| WO | 2005084595 A1 | 9/2005 |
| WO | 2006014233 A2 | 2/2006 |
| WO | 2006032051 A2 | 3/2006 |
| WO | 2006034008 A2 | 3/2006 |
| WO | 2006111391 A1 | 10/2006 |
| WO | 2006127089 A1 | 11/2006 |
| WO | 2006138173 A2 | 12/2006 |

(56) References Cited

FOREIGN PATENT DOCUMENTS

| WO | 2005102015 A3 | 4/2007 |
|---|---|---|
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008035337 A2 | 3/2008 |
| WO | 2008091515 A2 | 7/2008 |
| WO | 2008147964 A1 | 12/2008 |
| WO | 2008150529 A1 | 12/2008 |
| WO | 2009033469 A1 | 3/2009 |
| WO | 2009042196 A2 | 4/2009 |
| WO | 2009053497 A1 | 4/2009 |
| WO | 2009061389 A2 | 5/2009 |
| WO | 2009094188 A2 | 7/2009 |
| WO | 2009116041 A2 | 9/2009 |
| WO | 2009149462 A2 | 12/2009 |
| WO | 2010011699 A2 | 1/2010 |
| WO | 2010121076 A2 | 10/2010 |
| WO | 2013106585 A1 | 7/2013 |
| WO | 2015085218 A1 | 6/2015 |
| WO | 2018106837 A1 | 6/2018 |

OTHER PUBLICATIONS

H.R. Andersen "History of Percutaneous Aortic Valve Prosthesis," Herz No. 34. pp. 343-346. 2009.
Pavcnik, et al. "Development and initial Experimental Evaluation of a Prosthetic Aortic Valve for Transcatheter Placement," Cardiovascular Radiology, vol. 183, No. 1. pp. 151-154. 1992.
Bailey, S. "Percutaneous Expandable Prosthetic Valves," Textbook of Interventional Cardiology vol. 2, 2nd Ed. pp. 1268-1276. 1994.
Al-Khaja, et al. "Eleven Years' Experience with Carpentier-Edwards Biological Valves in Relation to Survival and Complications," European Journal of Cardiothoracic Surgery, vol. 3. pp. 305-311. 1989.
Sabbah, et al. "Mechanical Factors in the Degeneration of Porcine Bioprosthetic Valves: An Overview," Journal of Cardiac Surgery, vol. 4, No. 4. pp. 302-309. 1989.
Wheatley, "Valve Prostheses," Operative Surgery, 4th ed. pp. 415-424. 1986.
Uchida, "Modifications of Gianturco Expandable Wire Stents," American Journal of Roentgenology, vol. 150. pp. 1185-1187. 1986.
Walther T, Dehdashtian MM, Khanna R, Young E, Goldbrunner PJ, Lee W. Trans-catheter valve-in-valve implantation: in vitro hydrodynamic performance of the SAPIEN+cloth trans-catheter heart valve in the Carpentier-Edwards Perimount valves. Eur J Cardiothorac Surg. 2011;40(5):1120-6. Epub Apr. 7, 2011.
Fontaine, M.D., Arthur B., et al., "Vascular Stent Prototype; Results of Preclinical Evaluation", p. 29-34; Technical Developments and Instrumentation; Jan.-Feb. 1996, vol. 7, No. 1.
Fontaine, M.D., Arthur B., et al., "Prototype Stent: Invivo Swine Studies in the Biliary System1", p. 101-105, Journal of Vascular and Interventional Radiology; Jan.-Feb. 1997; vol. 8, No. 1.
Patrick W. Serruys, Nicolo Piazza, Alain Cribier, John Webb, Jean-Claude Laborde, Peter de Jaegere, "Transcatheter Aortic Valve Implantation: Tips and Tricks to Avoid Failure"; we file the table of contents and pp. 18 to 39 (Chapter 2) and pp. 102-114 (Chapter 8); the publication date according to the "Library of Congress Cataloging-in-Publication Data" is Nov. 24, 2009.

\* cited by examiner

FORCE LIMITING MECHANISM FOR PROSTHETIC HEART VALVE DELIVERY APPARATUS

CROSS-REFERENCE TO RELATED APPLICATION

This application is a continuation of PCT Patent Application No. PCT/US2020/040323, filed Jun. 30, 2020, which claims the benefit of U.S. Provisional Patent Application No. 62/870,372, filed Jul. 3, 2019, all of which applications are incorporated herein by reference.

FIELD

The present disclosure relates to mechanisms for limiting the amount of force that can be applied to implantable, expandable prosthetic devices, such as prosthetic heart valves.

BACKGROUND

The human heart can suffer from various valvular diseases. These valvular diseases can result in significant malfunctioning of the heart and ultimately require repair of the native valve or replacement of the native valve with an artificial valve. There are a number of known repair devices (e.g., stents) and artificial valves, as well as a number of known methods of implanting these devices and valves in humans. Percutaneous and minimally-invasive surgical approaches are used in various procedures to deliver prosthetic medical devices to locations inside the body that are not readily accessible by surgery or where access without surgery is desirable. In one specific example, a prosthetic heart valve can be mounted in a crimped state on the distal end of a delivery device and advanced through the patient's vasculature (e.g., through a femoral artery and the aorta) until the prosthetic valve reaches the implantation site in the heart. The prosthetic valve is then expanded to its functional size, for example, by inflating a balloon on which the prosthetic valve is mounted, actuating a mechanical actuator that applies an expansion force to the prosthetic valve, or by deploying the prosthetic valve from a sheath of the delivery device so that the prosthetic valve can self-expand to its functional size.

Prosthetic valves that rely on a mechanical actuator for expansion can be referred to as "mechanically expandable" prosthetic heart valves. The actuator typically takes the form of pull cables, sutures, wires and/or shafts that are configured to transmit expansion forces from a handle of the delivery apparatus to the prosthetic valve. When deploying a prosthetic valve, it is important to avoid exerting excessive radial force on the native annulus of the patient, which can rupture the native heart valve annulus.

SUMMARY

Described herein are embodiments of force limiting mechanisms for use with delivery assemblies that implant prosthetic devices. The force limiting mechanisms are primarily intended to limit the amount of force that can be applied to implantable, expandable prosthetic devices, such as prosthetic heart valves.

In a representative embodiment, a medical assembly can comprise a prosthetic heart valve and a delivery apparatus. The prosthetic heart valve can be radially expandable and compressible between a radially compressed configuration and a radially expanded configuration. The delivery apparatus can comprise a handle, at least one actuation member, and a force limiting mechanism. The actuation member can extend from the handle and can be coupled to the prosthetic valve. The actuation member can be configured to apply a proximally directed force to the prosthetic valve to cause the prosthetic valve to foreshorten axially and expand radially. The force limiting mechanism can be positioned within the handle and can comprise a pivot arm and a base portion. The pivot arm can be pivotably coupled to the base portion. The actuation member can be movably coupled to the pivot arm such that a force applied to the actuation member causes the pivot arm to pivot relative to the base portion. The force limiting mechanism can be configured to pinch the actuation member between the pivot arm and the base portion when the force applied to the actuation member exceeds a predetermined force, thereby preventing proximal movement of the actuation member. The force limiting member can permit proximal movement of the actuation member to produce radial expansion of the prosthetic valve when the force applied to the actuation member is less than the predetermined force.

In some embodiments, the pivot arm can be pivotably coupled to the base portion by a pin extending through a first end portion of the pivot arm and the base portion.

In some embodiments, the actuation member can extend around a pulley mounted on the arm. The pulley can pivot with the pivot arm upon application of the force to the actuation member. In some embodiments, the actuation member can extend between the arm and the base portion.

In some embodiments, the pulley can comprise a first pulley and the actuation member can further extend around a second pulley coupled to the handle and spaced from the pivot arm. In some embodiments, the second pulley can be positioned proximal to the pivot arm. In some embodiments, the base portion is connected to a first side of the handle and the second pulley is connected to a second side of the handle, the second side opposite the first side.

In some embodiments, the force limiting mechanism can further comprise a biasing member configured to exert a biasing force against the pivot arm. The biasing force can be selected such that when the force applied to the actuation member is less than the predetermined force, the pivot arm is prevented from pivoting against the biasing force, and when the force applied to the actuation member exceeds the predetermined force, the pivot arm pivots relative to the base portion.

In some embodiments, the biasing member can comprise a spring that is linearly expandable between a compressed configuration and an expanded configuration. One end portion of the spring can be coupled to the pivot arm and the other end portion of the spring can be coupled to the handle. In some embodiments, the spring can be configured such that a proximally directed force applied to the actuation member causes an expansion force to be applied to the spring.

In some embodiments, the spring can be configured such that, when the spring is in the compressed configuration, when the force applied to the actuation member is less than the predetermined force, the spring remains in the compressed configuration, and when the force applied to the actuation member exceeds the predetermined force, the spring expands to the expanded configuration.

In some embodiments, the spring can be configured such that, when the spring is in the expanded configuration, additional force greater than the predetermined force applied to the actuation member further pinches the actuation member between the pivot arm and the base portion, and when the force is removed from the actuation member, the spring contracts to the compressed configuration, which causes the pivot arm to pivot relative to the base portion such that the actuation member is released from between the pivot arm and the base portion.

In some embodiments, the force limiting mechanism can further comprise an adjustment mechanism configured to adjust the predetermined force.

In some embodiments, the adjustment mechanism can comprise an adjustment screw comprising a threaded portion that extends through the handle and is coupled to the biasing member. The adjustment screw can further comprise a screw head coupled to the threaded portion, the screw head arranged outside of the handle. The handle can include an internally threaded portion secured to an internal surface of the handle, the threaded portion having an internally threaded surface configured to engage with the threaded portion of the adjustment screw. In some embodiments, the adjustment screw is rotatable in a first direction which moves the adjustment screw further outside of the handle, pre-expands the biasing member, and increases the predetermined force. In some embodiments, the adjustment screw is rotatable in a second direction, opposite the first direction, which moves the adjustment screw into the handle and toward the pivot arm, moves the biasing member to a more relaxed state or a fully relaxed state, and decreases the predetermined force.

In some embodiments, the pivot arm is pivotably coupled to the base portion by a pivot element extending through a first end portion of the pivot arm and the base portion and the adjustment mechanism comprises a sliding element arranged within the pivot arm and coupled to the pivot element, the pivot element arranged within an elongate slot extending from the first end portion of the pivot arm, toward a second end portion of the pivot arm, the pivot element configured to slide along the slot in response to movement of the sliding element within the pivot arm. A position of the pivot element can determine a pivot point of the pivot arm and an arc length through which the pivot arm pivots in order to pinch the actuation member. In some embodiments, the sliding element includes an opening arranged around a rail coupled to the pivot arm, the sliding element configured to slide along the rail. Further, in some embodiments, the sliding element includes a threaded opening engaged with threads of a screw coupled to the pivot arm, the screw configured to rotate and cause linear translation of the sliding element along the rail and corresponding linear translation of the pivot element within the slot.

In some embodiments, the actuation member is one of a flexible cable, a suture, a wire, a cord, a flexible rod, and a flexible shaft.

In some embodiments, the delivery apparatus comprises a plurality of actuation members and a plurality of force liming mechanisms, wherein each force limiting mechanism is configured to interface with a corresponding one of the plurality of actuation members.

In some embodiments, the prosthetic heart valve is a mechanically expandable prosthetic heart valve including a plurality of interconnected struts, wherein the struts are pivotably coupled to one another at one or more pivot joints arranged along a length of each strut.

In another representative embodiment, a delivery apparatus for an implantable medical device can comprise a handle, at least one actuation member, and a force limiting mechanism within the handle. The actuation member can extend from the handle and can be coupled to the medical device. The actuation member can be configured to apply a proximally directed force to the medical device. The force limiting mechanism can comprise a pivot arm configured to limit the amount of proximally directed force that can be applied by the actuation member to the medical device.

In some embodiments, the pivot arm can be configured to prevent the actuation member from applying a proximally directed force to the medical device if a proximally directed force greater than a predetermined threshold is applied to the actuation member.

In some embodiments, the force limiting mechanism can further comprise a base portion and the pivot arm can be configured to pivot and retain the actuation member between the pivot arm and the base portion if a proximally directed force greater than the predetermined threshold is applied to the actuation member.

In some embodiments, the force limiting mechanism can further comprise a biasing member. The biasing member can be configured to exert a biasing force against the pivot arm and prevent pivoting of the arm if the proximally directed force applied to the actuation member is less than the predetermined threshold and permit pivoting of the pivot arm if the proximally directed force applied to the actuation member exceeds the predetermined threshold. In some embodiments, the biasing member can comprise a spring.

In some embodiments, the force limiting mechanism further comprises an adjustment screw including a threaded portion in threaded engagement with an internally threaded portion of the handle, where a first end of the threaded portion is coupled to the biasing member and a second end of the threaded portion is configured to be rotated in a first direction that increases the biasing force and an opposite, second direction that decreases the biasing force.

In some embodiments, the pivot arm includes an adjustable pivot element about which the pivot arm pivots relative to the base portion and the pivot element is configured to slide within an elongated slot of the pivot arm extending from a first end portion toward a second end portion of the pivot arm, in response to linear translation of a sliding element coupled to the pivot element and in sliding engagement with a portion of the pivot arm, in order to adjust a position of a pivot point of the pivot arm. In some embodiments, the sliding element is further coupled to a threaded portion of a screw arranged within the pivot arm via a threaded opening of the sliding element and the screw is rotatable to adjust a linear position of the sliding element within the pivot arm, between the first end portion and a location arranged between the first end portion and the second end portion, and correspondingly adjust the linear position of the pivot element within the elongated slot.

In some embodiments, the force limiting mechanism can further comprise a pulley mounted on the pivot arm and the actuation member can be routed at least partially around the pulley. In some embodiments, the actuation member can comprise a cable.

In some embodiments, the actuation member can be configured to produce radial expansion of the medical device upon application of the proximally directed force to the actuation member. In some embodiments, the actuation member can be configured to produce radial compression of the medical device upon application of the proximally directed force to the actuation member.

In some embodiments, the medical device is a mechanically expandable prosthetic heart valve including a plurality of interconnected struts, wherein the struts are pivotably coupled to one another at one or more pivot joints arranged along a length of each strut A representative method of implanting a prosthetic heart valve can comprise inserting into the body of a patient a distal end portion of a delivery apparatus and a prosthetic heart valve coupled to the distal end portion of the delivery apparatus in a radially compressed configuration, advancing the delivery apparatus distally until the prosthetic valve is disposed at a selected implantation site, and radially expanding the prosthetic valve. The delivery apparatus can comprise a handle, at least one actuation member, and a force limiting mechanism. The actuation member can extend from the handle and be coupled to the prosthetic valve and can be configured to apply a proximally directed force to the prosthetic valve to cause the valve to foreshorten axially and expand radially. The force limiting mechanism can be configured to limit the amount of proximally directed force that can be applied by the actuation member to the prosthetic valve. The prosthetic valve can be radially expanded by applying a proximally directed force to the actuation member so as to move the actuation member relative to the force limiting mechanism.

In some embodiments, the method can further comprise, when the proximally directed force applied to the at least one actuation member exceeds a predetermined force during the radially expanding the prosthetic valve, arresting movement of the at least one actuation member with the force limiting mechanism. Additionally, the method can further comprise, in response to the proximally directed force applied to the at least one actuation member exceeding the predetermined force, decreasing the amount of proximally directed force applied to the at least one actuation member so that it is less than the predetermined force, and then further moving the at least one actuation member relative to the force limiting mechanism. In some embodiments, arresting movement of the at least one actuation member with the force limiting mechanism includes pivoting a first end portion of a pivot arm of the force limiting mechanism into engagement with the at least one actuation member and pinching the at least one actuation member between the first end portion and a base portion of the force liming mechanism to which the pivot arm is coupled. In some embodiments, further moving the at least one actuation member relative to the force limiting mechanism includes moving the first end portion of the pivot arm out of engagement with the at least one actuation member and allowing the at least one actuation member to slide relative to the pivot arm.

In some embodiments, arresting movement of the at least one actuation member includes stopping radially expanding the prosthetic heart valve.

Another representative method for limiting a force applied to an implantable medical device by an actuation member of a delivery apparatus can comprise applying a proximally directed force to the medical device with the actuation member, the actuation member coupled to the medical device and extending into a handle of the delivery apparatus. The method can further comprise, in response to the proximally directed force being less than a predetermined threshold, spacing a first end portion of a pivot arm of a force limiting mechanism of the delivery apparatus away from the actuation member and allowing the actuation member to continue to apply the proximally directed force to the medical device. The method can further comprise, in response to the proximally directed force being greater than the predetermined threshold, pivoting the first end portion of the pivot arm toward the actuation member and a base portion to which the pivot arm is coupled and configured to pivot around and pinching the actuation member between the first end portion of the pivot arm and the base portion to arrest movement of the actuation member.

In some embodiments, applying the proximally directed force to the medical device includes radially expanding the medical device. In some embodiments, the medical device is a mechanically expandable prosthetic heart valve.

In some embodiments, spacing the first end portion of the pivot arm away from the actuation member and allowing the actuation member to continue to apply the proximally direction force includes maintaining a second end portion of the pivot arm proximate to the base portion with a biasing element coupled between the second end portion and an internal surface of the handle. In some embodiments, the biasing element is configured to remain in a compressed state when the proximally directed force is less that the predetermined threshold and expand into an expanded state when the proximally directed force is greater than the predetermined threshold, where in the expanded state, the second end portion pivots away from the base portion and the first end portion pivots into engagement with the actuation member to arrest movement of the actuation member.

In some embodiments, pivoting the first end portion of the pivot arm toward the actuation member and pinching the actuation member between the first end portion and the base portion includes pivoting the pivot arm about a pivot element coupling the pivot arm to the base portion.

In some embodiments, the method can further comprise adjusting a location of the pivot element, between the first end portion and the second end portion, to adjust an arc length through which the pivot arm pivots in order to pinch the actuation member and adjust the predetermined threshold. In some embodiments, adjusting the location of the pivot element includes sliding the pivot element within an elongated slot arranged in the pivot arm, the elongated slot extending between the first end portion of the pivot arm and a location between the first end portion and the second end portion.

In some embodiments, the method can further comprise adjusting the predetermined threshold to adjust a maximum amount of force that can be applied to the medical device, during the applying the proximally directed force. In some embodiments, adjusting the predetermined force includes actuating an adjustment mechanism coupled to the biasing element to pre-expand the biasing member to increase a biasing force applied to the second end portion of the pivot arm and increase the predetermined threshold. In some embodiments, adjusting the predetermined threshold includes actuating the adjustment mechanism coupled to the biasing element to move the biasing member into a more relaxed or fully relaxed state to decrease the biasing force and decrease the predetermined threshold. In some embodiments, adjusting the predetermined threshold includes: rotating a screw coupled to an end of the biasing member and in threaded engagement with an inner surface of the handle in a first direction to move the screw away from an end of the biasing element coupled to the pivot arm and increase the predetermined threshold; and rotating the screw in an opposite, second direction to move the screw toward the end of the biasing element coupled to the pivot arm and decrease the predetermined threshold.

The foregoing and other objects, features, and advantages of the invention will become more apparent from the following detailed description, which proceeds with reference to the accompanying figures.

DETAILED DESCRIPTION

Described herein are embodiments of a method and apparatus to limit a force that can be applied to a radially expandable prosthetic device, such as a prosthetic heart valve. Disclosed embodiments include a method and apparatus that can limit an expansion force that can be applied to a prosthetic heart valve, such as during deployment of the prosthetic valve in the body. Prosthetic valves disclosed herein can be radially compressible and expandable between a radially compressed configuration and a radially expanded configuration. Thus, the prosthetic valves can be crimped on an implant delivery apparatus in the radially compressed configuration during delivery, and then expanded to the radially expanded configuration once the prosthetic valve reaches the implantation site.

Figure 1:
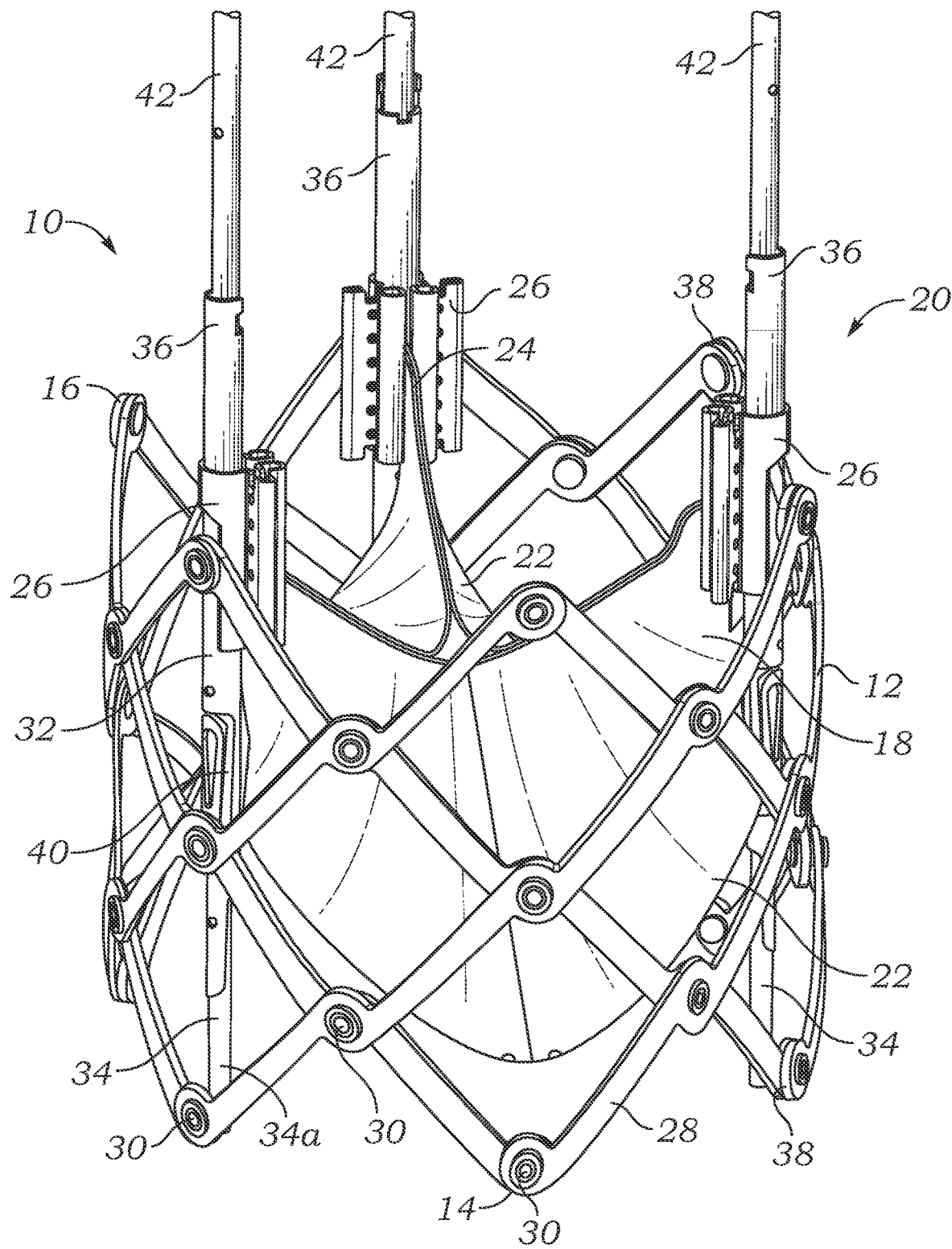
FIG. 1 is a perspective view of an exemplary embodiment of a prosthetic heart valve.

FIG. 1 shows an exemplary prosthetic valve 10, according to one embodiment. The prosthetic valve 10 can be radially compressible and expandable between a radially compressed configuration for delivery into a patient (see e.g., FIG. 3) and a radially expanded configuration (see e.g., FIGS. 1 and 4). In particular embodiments, the prosthetic valve 10 can be implanted within the native aortic annulus, although it also can be implanted at other locations in the heart, including within the native mitral valve, the native pulmonary valve, and the native tricuspid valve. The prosthetic valve 10 can include an annular stent or frame 12 having a first end 14 and a second end 16.

In the depicted embodiments, the first end 14 is an inflow end and the second end 16 is an outflow end. The outflow end 16 can be coupled to a delivery apparatus for delivering and implanting the prosthetic valve within the native aortic valve in a transfemoral, retrograde delivery approach. In other embodiments, the inflow end 14 can be coupled to the delivery apparatus, depending on the particular native valve being replaced and the delivery technique that is used (e.g., transfemoral, transapical, etc.).

The prosthetic valve 10 can also include a valvular structure 18 which is coupled to the frame 12 and configured to regulate the flow of blood through the prosthetic valve 10 from the inflow end to the outflow end. The prosthetic valve 10 can further include a plurality of actuators 20 mounted to and equally spaced around the inner surface of the frame 12.

Each of the actuators 20 can be configured to form a releasable connection with one or more respective actuators of a delivery apparatus, as further described below.

The valvular structure 18 can include, for example, a leaflet assembly comprising one or more leaflets 22 (there are three leaflets 22 in the illustrated embodiment) made of a flexible material. The leaflets 22 of the leaflet assembly can be made from, in whole or part, biological material, biocompatible synthetic materials, or other such materials. Suitable biological material can include, for example, bovine pericardium (or pericardium from other sources). The leaflets 22 can be arranged to form commissures 24, which can be, for example, mounted to respective actuators 20. Further details regarding transcatheter prosthetic heart valves, including the manner in which the valvular structure can be coupled to the frame 12 of the prosthetic valve 10, can be found, for example, in U.S. Pat. Nos. 6,730,118, 7,393,360, 7,510,575, 7,993,394, 8,652,202, and U.S. Patent Publication 2018/0325665, all of which are incorporated herein by reference in their entireties.

In some embodiments, the prosthetic valve 10 can include a plurality of commissure support elements configured as commissure clasps or clamps 26. In the illustrated configuration, the prosthetic valve 10 includes a commissure clamp 26 positioned at each commissure 24 and configured to grip adjacent portions of two leaflets 22 at each commissure 24 at a location spaced radially inwardly of the frame 12. Each clamp 26 can be mounted on an actuator 20 as shown. In alternative embodiments, the commissure support elements (such as clamps 26) can be mounted to the struts 28 of the frame, or alternatively, the commissures 24 can be mounted (e.g., sutured) directly to the struts of the frame. Further details of the commissure clamps 26 and other techniques for mounting the commissures of a valve assembly to a frame can be found in U.S. Patent Publication No. 2018/0325665.

Although not shown, the prosthetic valve 10 can also include one or more skirts or sealing members. For example, the prosthetic valve 10 can include an inner skirt mounted on the inner surface of the frame. The inner skirt can function as a sealing member to prevent or decrease perivalvular leakage, to anchor the leaflets 22 to the frame, and/or to protect the leaflets against damage caused by contact with the frame during crimping and during working cycles of the prosthetic valve. The prosthetic valve 10 can also include an outer skirt mounted on the outer surface of the frame 12. The outer skirt can function as a sealing member for the prosthetic valve by sealing against the tissue of the native valve annulus and helping to reduce perivalvular leakage past the prosthetic valve. The inner and outer skirts can be formed from any of various suitable biocompatible materials, including any of various synthetic materials (e.g., polyethylene terephthalate (PET)) or natural tissue (e.g., pericardial tissue). The inner and outer skirts can be mounted to the frame using sutures, an adhesive, welding, and/or other means for attaching the skirts to the frame.

The frame 12 can be made of any of various suitable materials, such as stainless steel, a cobalt chromium alloy, or a nickel titanium alloy ("NiTi"), for example Nitinol. Referring again to FIG. 1, as shown, the frame 12 can include a plurality of interconnected struts 28 arranged in a lattice-type pattern. The struts 28 are shown as positioned diagonally, or offset at an angle relative to, and radially offset from, a longitudinal axis of the prosthetic valve 10 when the prosthetic valve is in the expanded configuration. In other implementations, the struts 28 can be offset by a different amount than depicted in FIG. 1, or some or all of the struts 28 can be positioned parallel to the longitudinal axis of the prosthetic valve 10.

In the illustrated embodiment, the struts 28 are pivotably coupled to one another at one or more pivot joints along the length of each strut. For example, in the illustrated configuration, each of the struts 28 can be formed with apertures (see e.g., apertures 114 in FIG. 4) at opposing ends of the strut and with apertures spaced along the length of the strut. Respective hinges can be formed at the locations where struts 28 overlap each other via fasteners or pivot members, such as rivets or pins 30 that extend through the apertures. The hinges can allow the struts 28 to pivot relative to one another as the frame 12 is radially expanded or compressed, such as during assembly, preparation, or implantation of the prosthetic valve 10.

In some embodiments, the frame 12 can be constructed by forming individual components (e.g., the struts and fasteners of the frame) and then mechanically assembling and connecting the individual components together. In other embodiments, the struts 28 are not coupled to each other with respective hinges but are otherwise pivotable or bendable relative to each other to permit radial expansion and contraction of the frame 12. For example, the frame 12 can be formed (e.g., via laser cutting, electroforming or physical vapor deposition) from a single piece of material (e.g., a metal tube). Further details regarding the construction of the frame and the prosthetic valve are described in U.S. Patent Publication Nos. 2018/0153689, 2018/0344456, and 2019/0060057, all of which are incorporated herein by reference. Additional examples of expandable prosthetic valves that can be used with the delivery apparatuses disclosed herein are described in U.S. Pat. Nos. 9,700,442 and 9,827,093, which are incorporated herein by reference.

Referring still to FIG. 1, in some embodiments, the prosthetic valve 10 can comprise one or more actuators 20 configured to produce radial expansion and compression of the frame 12. The one or more actuators in the illustrated embodiment comprise one or more push-pull mechanisms 32 coupled to the frame 12. In the illustrated embodiment, the prosthetic valve 10 has three push-pull mechanisms 32, however, in other embodiments a greater or fewer number of push-pull mechanisms 32 can be used.

Each push-pull mechanism 32 can generally comprise an inner member 34, such as an inner tubular member, and an outer member 36 disposed about the inner member 34. The inner members 34 and the outer members 36 can be movable longitudinally relative to each other in a telescoping manner to radially expand and contract the frame 12, as further described in U.S. Patent Publications Nos. 2018/0153689 and 2018/0325665, which are incorporated herein by reference. The inner members 34 can be, for example, rods, cables, wires, or tubes. The outer members 36 can be, for example, tubes or sheaths having sufficient rigidity such that they can apply a distally directed force to the frame without bending or buckling.

The inner members 34 can have distal end portions 34a coupled to the inflow end 14 of the frame 12 (e.g., with a coupling element such as a pin member 30). In the illustrated embodiment, each of the inner members 34 are coupled to the frame at respective apices 38 at the inflow end 14 of the frame 12. For example, the distal end portion 34a of each inner member 34 can be pivotably connected to the rivet or pin 30 that connects the two struts at the adjacent apex 38. The outer members 36 can be coupled to apices 38 at the outflow end 16 of the frame 12 at, for example, a mid-portion of the outer member 36, as shown in FIG. 1, or at a proximal end portion of the outer member, as desired. The outer members 36 can be pivotably connected to the rivet or pin 30 that connects the two struts at the adjacent apex 38.

The inner member 34 and the outer member 36 can telescope relative to each other between a fully contracted state (corresponding to a fully radially expanded state of the prosthetic valve) and a fully extended state (corresponding to a fully radially compressed state of the prosthetic valve). In the fully extended state, the inner member 34 is fully extended from the outer member 36. In this manner, the push-pull mechanisms 32 allow the prosthetic valve 10 to be fully expanded or partially expanded to different diameters and retain the prosthetic valve in the partially or fully expanded state.

In use, a delivery apparatus can be releasably coupled to the push-pull mechanisms 32 of prosthetic valve 10. For example, the delivery apparatus can have one or more actuator assemblies that are releasably coupled to respective push-pull mechanisms 32 of the prosthetic valve. The actuators of the delivery apparatus can be configured to transfer pushing and/or pulling forces from a handle of the delivery apparatus to the push-pull mechanisms 32 of the prosthetic valve. Each of the actuator assemblies of the delivery apparatus can include an inner member 42 that is releasably coupled to a respective inner member 34 of a push-pull mechanism 32. Each actuator assembly of the delivery apparatus can also include an outer member (not shown) that is releasably coupled to a respective outer member 36 of a push-pull mechanism 32.

Once coupled to the delivery apparatus, the prosthetic valve 10 can then be radially collapsed (see e.g., FIG. 3) and the distal end portion of the delivery apparatus, along with the radially collapsed valve, can be inserted into a patient. Once the prosthetic valve 10 is at the desired implantation site, the prosthetic valve can be radially expanded (see e.g., FIG. 4). In some embodiments, as shown in FIG. 1, the push-pull mechanisms 32 can comprise one or more locking mechanisms 40, allowing the frame 12 to maintain an expanded diameter after the prosthetic valve is released from the delivery apparatus. Additional details of the locking mechanism can be found in U.S. Patent Publication No. 2018/0153689.

Figure 2:
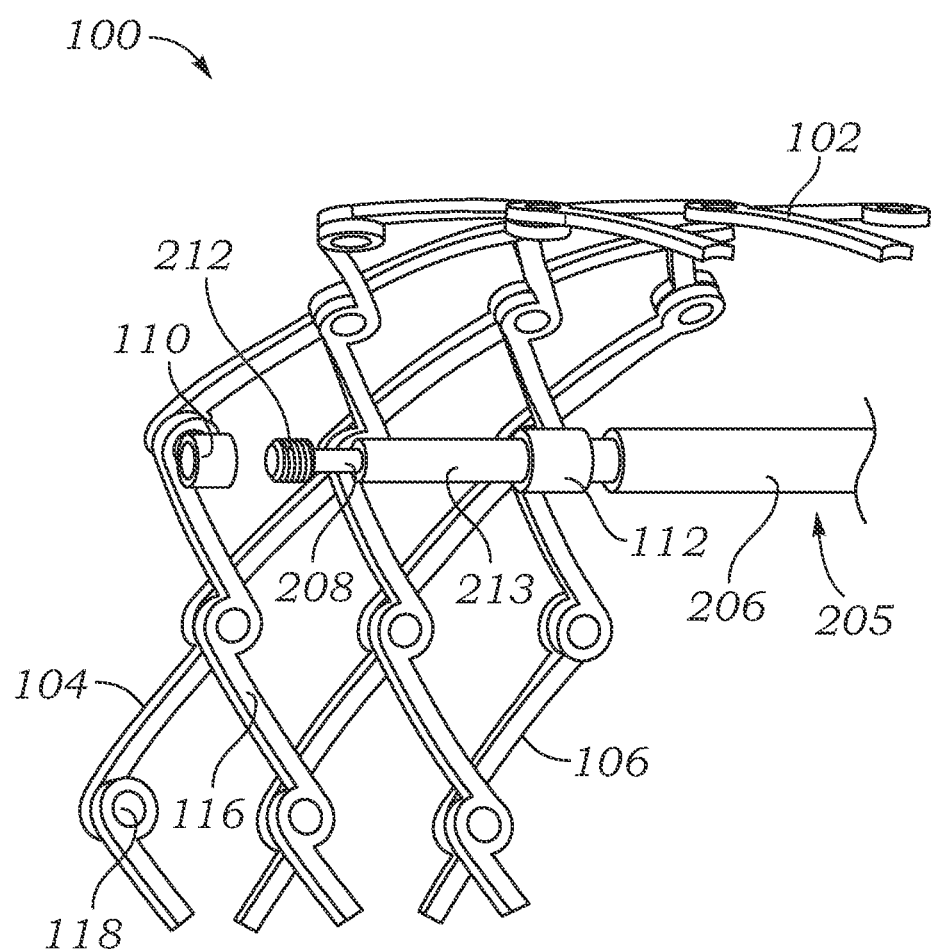
FIG. 2 is a perspective view of a portion of another exemplary embodiment of a prosthetic heart valve.

FIG. 2 illustrates another embodiment of a prosthetic valve 100 comprising a frame 102. The prosthetic valve 100 can include leaflets 18 and inner and/or outer skirts as previously described, although these components are omitted for purposes of illustration. The frame 102 comprises a plurality of struts 116 formed with apertures 114 (see FIG. 4) and pivot members 118 (e.g., pins or rivets) connecting the struts to each other to form a plurality of pivot joints. The frame 102 can have the same construction as the frame 12, except that the frame 102 includes struts 116 that are longer than struts 28 of frame 12. The longer struts 116 form more pivot joints along the length of each strut and more openings or cells of the frame compared to the struts 28.

The prosthetic valve 100 is configured to be releasably coupled to one or more actuator assemblies 205 of a delivery apparatus 200 (further described below) to produce radial expansion and compression of the frame 102. To such ends, the prosthetic valve 100 can include one or more nuts or threaded sleeves 110 affixed to the frame 102, such as at an inflow portion 104 of the frame 102. The prosthetic valve 100 can further comprise one or more stoppers 112 affixed to the frame 102, such as at an outflow portion 106 of the frame. In the illustrated embodiment, the sleeve 110 is circumferentially aligned with the stopper 112. However, in other embodiments, the sleeve 110 can be circumferentially offset from the stopper 112.

The actuator assemblies 205 can be used to radially expand the prosthetic valve 100 from a radially compressed state to a radially expanded state at an implantation site within a patient's body, as further described below. In some embodiments, the prosthetic valve 100 can further include one or more locking mechanisms (not shown), for example, a locking screw and a nut, that maintain the prosthetic valve in an expanded configuration. After the frame 102 is expanded to a desired radially expanded size, the locking mechanism can be actuated or can self-actuate to lock the frame 102 in the desired radially expanded size. The actuator assemblies 205 can then be released from the prosthetic valve 100 and removed from the body. Further details of the actuator assemblies and the locking mechanism can be found in U.S. Patent Publication 2018/0153689.

Figure 3:
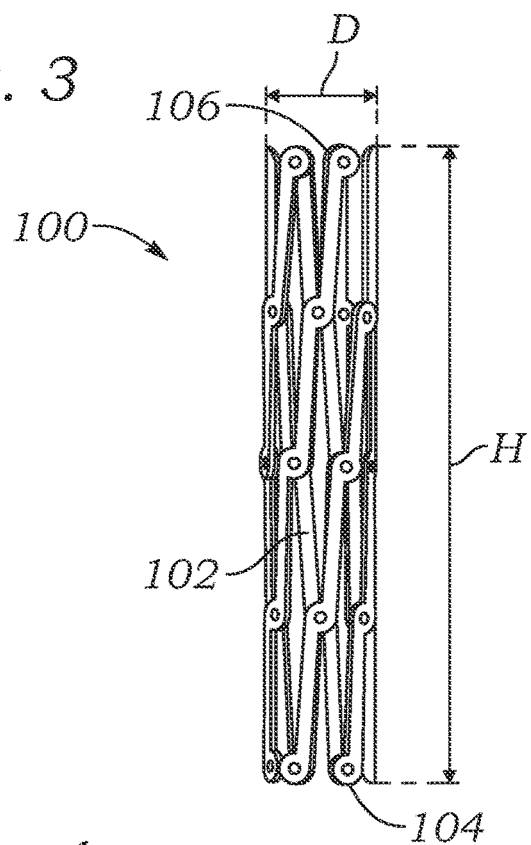
FIG. 3 is a side view of the frame of the prosthetic heart valve of FIG. 2 shown in a radially collapsed configuration.
Figure 4:
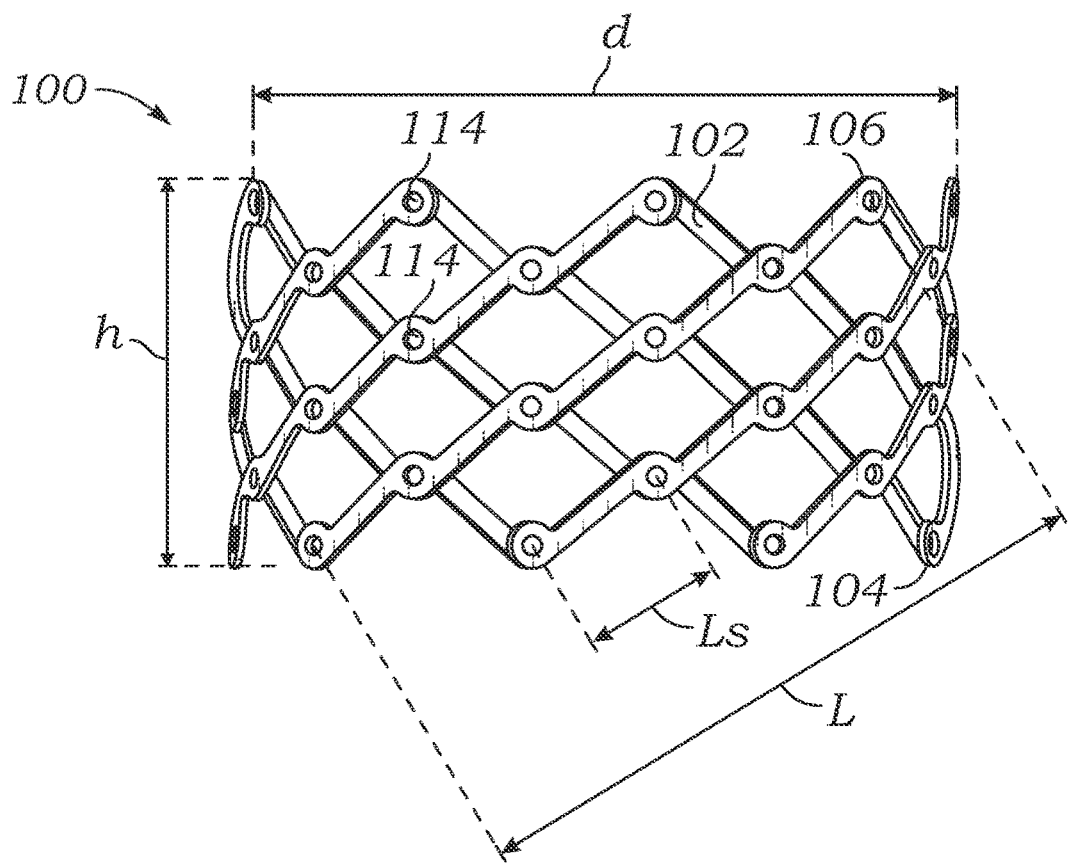
FIG. 4 is a side view of the prosthetic heart valve of FIG. 2 shown in a radially expanded configuration.

FIGS. 3-4 illustrate the bare frame 102 (without the leaflets and other components) of the prosthetic valve 100 for purposes of illustrating expansion of the prosthetic valve from the radially compressed configuration to the radially expanded configuration. FIG. 3 shows the frame 102 in the radially compressed configuration, and FIG. 4 shows the frame 102 in the fully radially expanded configuration. The prosthetic valve 100 in the illustrated configuration can be radially expanded by maintaining the first end 104 of the frame 102 at a fixed position while applying a force in the axial direction against the second end 106 toward the first end 104. Alternatively, the prosthetic valve 100 can be expanded by applying an axial force against the first end 104 while maintaining the second end 106 at a fixed position, or by applying opposing axial forces to the first and second ends 104, 106, respectively.

Figure 5:
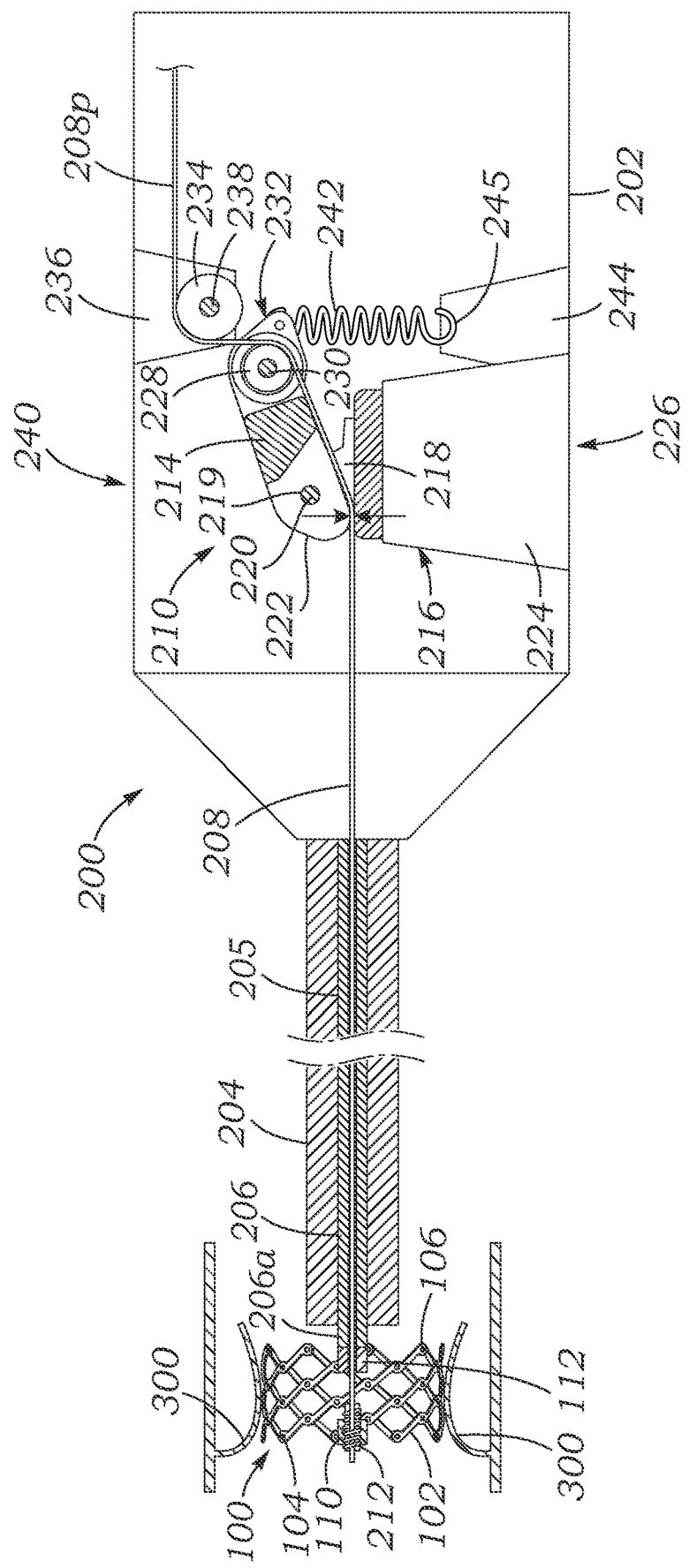
FIG. 5 is an exemplary prosthetic valve delivery apparatus shown being used to implant the prosthetic heart valve of FIG. 2.

FIG. 5 illustrates a delivery apparatus 200, according to one embodiment, adapted to deliver a prosthetic heart valve, such as the illustrated prosthetic heart valve 100, described above. The prosthetic valve 100 can be releasably coupled to the delivery apparatus 200, as further described below. It should be understood that the delivery apparatus 200 and other delivery apparatuses disclosed herein can be used to implant prosthetic devices other than prosthetic valves, such as stents or grafts.

The delivery apparatus 200 in the illustrated embodiment generally includes a handle 202, a first elongated shaft 204 (which comprises an outer shaft in the illustrated embodiment) extending distally from the handle 202, at least one actuator assembly 205 extending distally through the outer shaft 204, and a force limiting mechanism 210 within the handle 202. The handle 202 and the force limiting mechanism 210 inside the handle is enlarged in FIG. 5 for purposes of illustration. The handle 202 typically has a diameter suitable to allow a user to grasp the handle with the user's hand. The at least one actuator assembly 205 can comprise an inner shaft 206 and an actuation member 208 extending through the inner shaft 206. The inner shaft 206 can have a distal end portion 206a that extends distally beyond the distal end of the outer shaft 204.

In the illustrated embodiment, only one actuator assembly 205 is shown. However, the delivery apparatus 200 can include a plurality of actuator assemblies 205, which can be circumferentially spaced apart from each other and can extend axially through the outer shaft 204 from the handle 202 to the prosthetic valve 100. The prosthetic valve 100 can include a pair of a sleeve 110 and a stopper 112 for each actuator assembly 205. Similarly, only one force limiting mechanism 210 is shown in the illustrated embodiment. However, in alternative embodiments, a force limiting mechanism 210 can be provided for each actuator assembly 205 where multiple actuator assemblies are provided.

In the following description, reference is made to a single actuator assembly 205. However, it should be understood that the description also applies to each actuator assembly where multiple actuator assemblies are present. The actuation member 208 can extend through the handle 202, and through the inner shaft 206 and can be coupled to a screw 212 at a distal end portion of the actuation member 208. The screw 212 can be configured to be received in and threadably engage internal threads of the nut 110 so as to releasably couple the delivery apparatus 200 to the prosthetic valve 100, as shown in FIG. 5. As such, a proximally directed force applied to the actuation member 208 applies a proximally directed force to the distal end portion 104 of the prosthetic valve 100.

In some embodiments, as shown in FIG. 2, the actuator assembly 205 can further comprise a cover tube 213 disposed around the actuation member 208 and extending through the inner shaft 206 from the prosthetic valve to the handle. The actuation member 208 can comprise any member configured to transfer a proximally directed pulling force from the handle 202 to the prosthetic valve 100 to produce radial expansion of the prosthetic valve 100, as described above. The actuation member 208 desirably is sufficiently flexible so that it can be reeved around one or more pulleys of a force limiting mechanism 210, as described in detail below. The actuation member 208 can comprise, for example, a flexible cable, a suture (e.g. a single filament suture or a multi-filament suture), a wire, a cord, a flexible rod, or a flexible shaft. In particular embodiments, actuation member 208 comprises a flexible cable formed from a plurality of helically twisted filaments or wires (e.g., metal wires or filaments).

As further shown in FIG. 2, the actuation member 208 and the cover tube 213 can extend through the stopper 112. The inner shaft 206 can annularly surround the cover tube 213. The stopper 112 can have an annular inner surface with an inner diameter larger than the outer diameter of the cover tube 213 and the screw 212 such that the cover tube 213 and the screw 212 can be retracted through the stopper 112 after the frame 102 is expanded and the delivery apparatus 200 is disconnected from the frame. The stopper 112 is sized to abut or engage the distal end 206a of the inner shaft 206 such that the inner shaft is prevented from moving distally beyond the stopper. The cover tube 213 facilitates passage of the screw 212 through the stopper 112.

Although the prosthetic valve 100 in the illustrated embodiment is shown as having only one pair of a nut 110 and a corresponding stopper 112 for coupling with a respective actuator assembly 205 of the delivery apparatus 200, it should be understood that a pair of a nut 110 and a stopper 112 can be provided for each actuator assembly. Each pair of a nut 110 and a stopper 112 can be mounted to the frame 102 at circumferentially spaced apart locations.

In some embodiments, the outer shaft 204 of the delivery apparatus 200 can be configured as a steerable guide catheter having an adjustable curvature for use in steering the delivery apparatus through a patient's vasculature. A steering or pull wire (not shown) can extend through the outer shaft 204 and can have a distal end fixed at a location along the distal section and a proximal end operatively connected to an adjustment mechanism, for example, a knob on the handle 202. Further details of steering mechanisms that can be incorporated in the delivery apparatus can be found in U.S. Pat. Nos. 9,061,119 and 10,076,638, which are incorporated herein by reference.

In some embodiments, the outer shaft 204 and the actuator assembly 205 can be moved relative to one another (axially and/or rotationally) to facilitate delivery and positioning of the prosthetic valve 100 at an implantation site in the patient's body. The handle 202 can include an adjustment mechanism configured to produce relative movement between the outer shaft 204 and the actuator assembly 205. For example, the handle 202 can include a slidable or rotatable adjustment knob that is operatively connected to the actuator assembly 205 and configured to produce axial movement of the actuator assembly 205 in the proximal and distal directions relative to the outer shaft 204.

In some embodiments, the distal end portion of the outer shaft 204 can form a sheath that is sized and shaped to receive and house the prosthetic valve 100 in a radially compressed state for delivery into and through a patient's vasculature. Once the prosthetic valve 100 is advanced to the implantation site or adjacent the implantation site, the prosthetic valve can be advanced from the outer shaft 204 by advancing the actuator assembly 205 relative to the outer shaft 204, after which the prosthetic valve can be radially expanded. In alternative embodiments, the outer shaft 204 can be configured to move axially relative to the inner shaft 206 such as by operating a knob on the handle 202. The knob can be operatively connected to the proximal end portion of the outer shaft 204 and can be configured to retract the outer shaft 204 proximally relative to the inner shaft 206 to deploy a prosthetic valve from the distal end of the sheath.

As shown in FIG. 5, a medical assembly can comprise the delivery apparatus 200 and the prosthetic valve 100 coupled to the distal end of the delivery apparatus. When the prosthetic valve 100 is coupled to the delivery apparatus 200, the distal end portion 206a of the inner shaft 206 can abut a corresponding stopper 112 of the frame 102. The stopper 112 is sized to prevent the inner shaft 206 from moving distally beyond the stopper 112. When the distal end portion 206a of the inner shaft 206 abuts the stopper 112 of the frame 102 and a proximally directed force is applied to the actuation member 208, the stopper 112 prevents the proximal end portion 106 of the frame 102 from moving while the distal end portion 104 of the frame 102 is moved proximally by the actuation member 208, thereby causing the frame 102 to foreshorten axially and expand radially.

As noted above, the screw 212 can be screwed into a corresponding nut 110 on the frame 102 to effectively couple the prosthetic valve 100 to the delivery apparatus 200. Once the prosthetic valve 100 has been radially expanded at the desired implantation location, the screw 212 can be removed from the nut 110 by rotating the actuation member 208 to unscrew the screw 212 from the nut 110 so as to release the prosthetic valve from the delivery apparatus 200. The stopper 112 can have an annular inner surface with an inner diameter larger than the outer diameter of the cover tube 213 and the screw 212 such that the actuation member 208, the cover tube 213 and the screw 212 can be retracted through the stopper 112 after the frame 102 is expanded and the actuation member 208 is disconnected from the frame by unscrewing the screw 212 from the nut 110.

The proximal end portion of the actuation member 208 can be operatively connected to a control mechanism, such as a control knob on the handle 202, that allows a doctor or operator of the delivery apparatus 200 to rotate the actuation member 208 (e.g., to unscrew the screw 212 from the nut 110) and/or to pull the actuation member 208 axially relative to the inner shaft 206 to apply a proximally directed force to distal end portion 104 of the frame 102 during valve expansion. For example, the control knob can be a manually rotatable knob that is effective to pull the actuation member 208 proximally when rotated by a user. In another embodiment, the actuation member 208 can be operatively connected to a motor (which can be housed inside the handle 202) that is operable to pull the actuation member 208 proximally when actuated by a user, such as by pressing a button or switch on the handle. The delivery apparatus can include another motor (which can be housed inside the handle 202 and actuated by a respective button or switch) to produce rotation of the actuation member 208 for disconnecting the screw 212 from the nut 110.

When expanding the prosthetic valve 100 by applying a proximally directed force to the distal end portion 104 of the frame 102 as described above, if too great a force is applied, it is possible to overload the patient's annulus, which risks annular rupture. It is also possible that applying too great of a force to the frame 102 can damage the components of the delivery apparatus 200, which risks delivery system failure during an implantation procedure. Accordingly, it can be desirable to limit the amount of force that can be applied to the frame 102 while expanding the prosthetic valve 100. The force limiting mechanism 210 can limit the amount of force that can be applied to expand the prosthetic valve 100, as explained in further detail below, to limit these potential risks.

Figure 6:
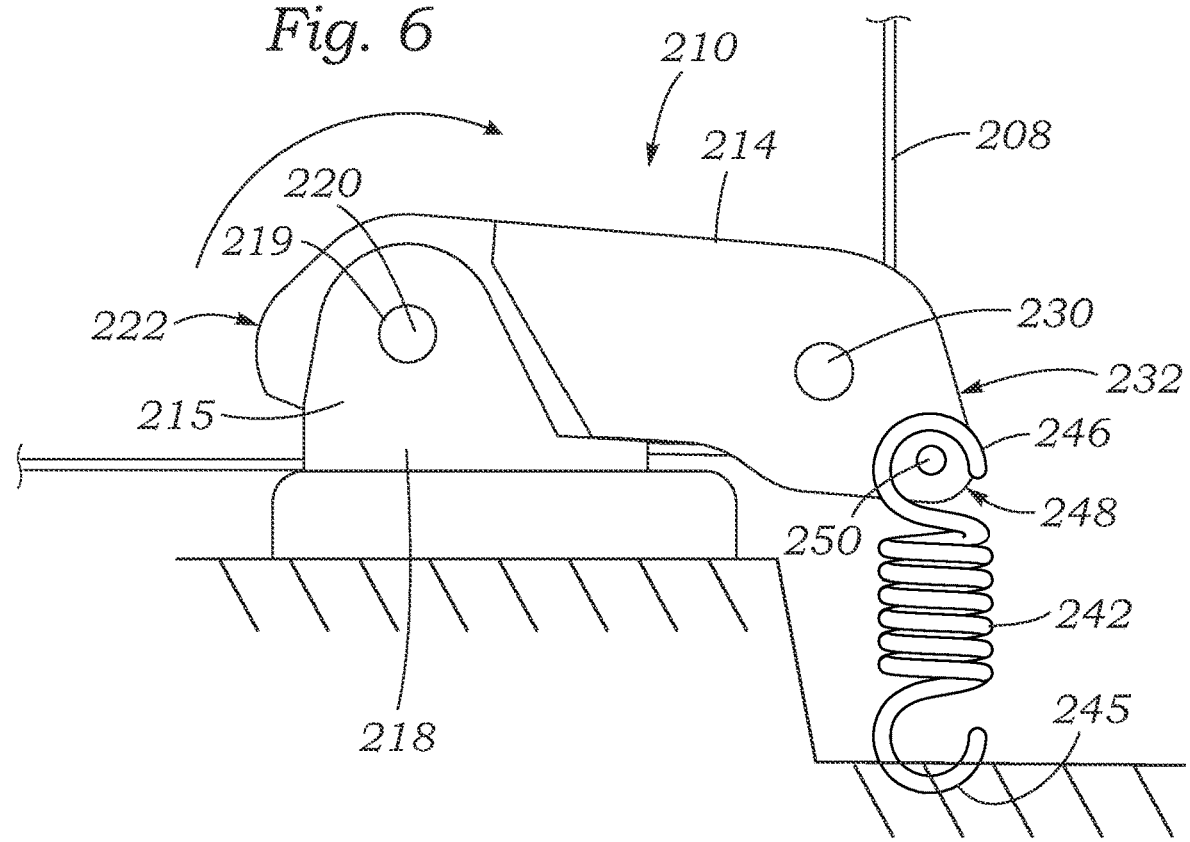
FIG. 6 is a side view of an exemplary force limiting mechanism of the delivery apparatus of FIG. 5.
Figure 7:
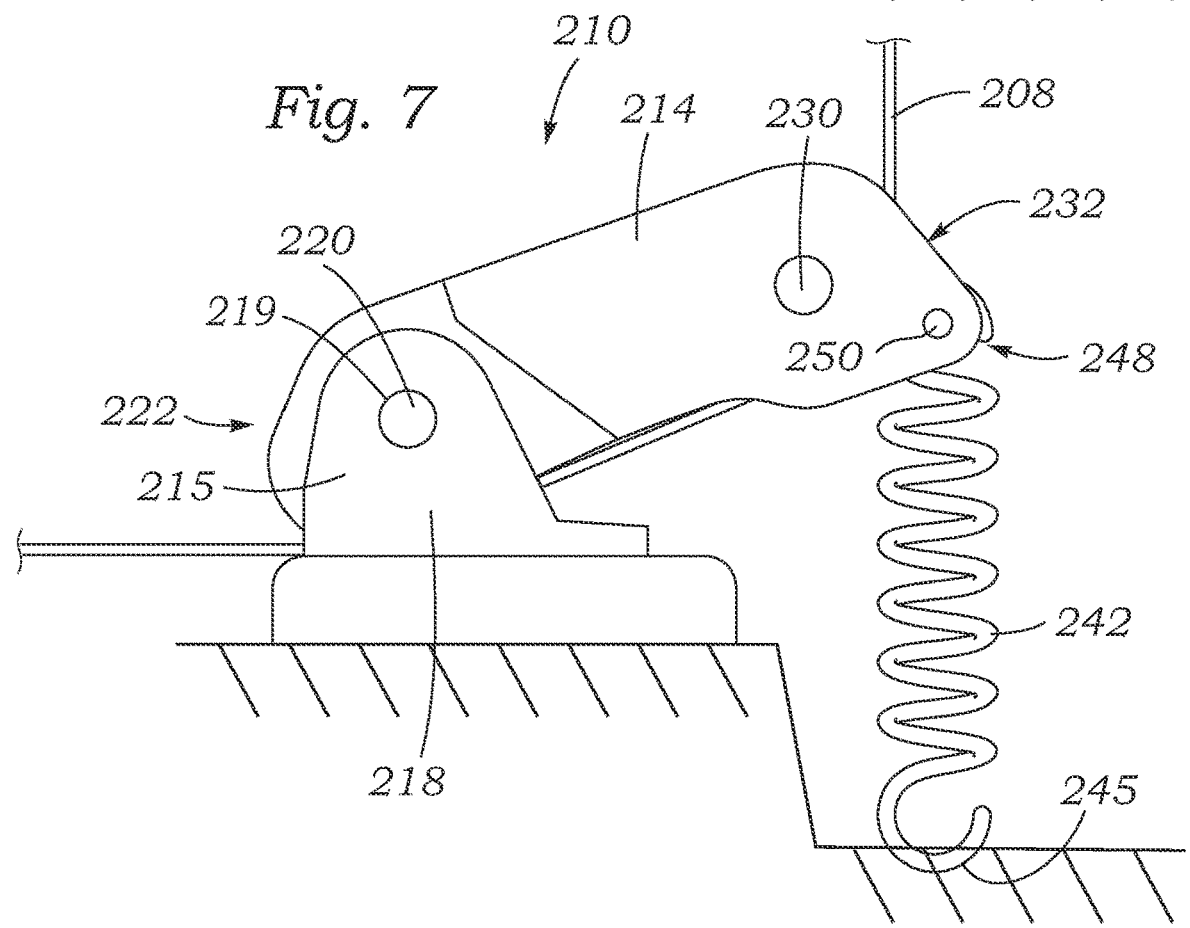
FIG. 7 is another side view of the exemplary force limiting mechanism of FIG. 6.

Referring to FIG. 5, the force limiting mechanism 210 can be located inside the handle 202 and can comprise a pivot arm 214 pivotably coupled to a base portion 216 for pivoting movement relative to the base portion. The base portion 216 can have an upper portion 218 and a lower portion 224. The lower portion 224 of the base portion 216 can be connected to a first side 226 of the handle 202 such that the position of the base portion 216 is fixed with respect to the handle 202. The upper portion 218 of the base portion 216 can have two ears 215 that extend away from the lower portion 224 (FIGS. 6 and 7 show one ear of the upper portion 218) such that the arm 214 can be positioned between the ears 215 of the upper portion 218.

The ears 215 of the upper portion 218 can each have an opening 219 through which a pin or pivot element 220 can be extended. A first end portion 222 of the arm 214 can have an opening extending therethrough that can be aligned with the openings 219 in the ears 215 of the upper portion 218 such that the pin 220 can extend through the ears 215 of the upper portion 218 and through the first end portion 222 of the arm 214, thereby coupling the arm 214 to the base portion 216. The pin 220 can create an axis about which the arm 214 can pivot. This axis can be orthogonal to a longitudinal axis of the prosthetic valve 100.

The force limiting mechanism 210 can further comprise a first pulley 228, as best shown in FIG. 5, coupled to a second end portion 232 of the arm 214 via a first pulley pin or shaft 230 that can extend through the second end portion 232 of the arm 214. In the illustrated embodiment, the first pulley 228 is positioned within the interior of the arm 214 and is free to rotate around the pin 230 within the arm.

In the illustrated embodiment, a second pulley 234 can be positioned within the handle 202 and can be laterally and axially offset from the arm 214 as shown in FIG. 5 (e.g., the second pulley 234 can be positioned proximal to the arm 214 and axially further from the base portion 216 than the arm 214). A pulley support member 236 can be connected to a second side 240 of the handle 202, opposite the first side 226. A second pulley pin or shaft 238 can be connected to the support member 236 and can extend through the second pulley 234 such that the second pulley 234 is free to rotate around the second pulley pin 238.

In the illustrated embodiment, within the handle 202, the actuation member 208 is routed underneath the arm 214 between the arm and the base portion 216, partially around the first pulley 228 and partially around the second pulley 234. The proximal end portion 208p of the actuation member 208, proximal to the force limiting mechanism 210, can then be routed and operatively connected to a control mechanism (e.g., a knob or motor) that can allow an operator of the delivery apparatus 200 to apply a proximally directed force to the actuation member 208 to expand the prosthetic valve 100, as described above. Because of the routing of the actuation member 208 around the first and second pulleys 228, 234, when a proximally directed force is applied to the actuation member 208, a pivoting force is applied to the arm 214 (that is, a force applied in a direction to cause the arm to pivot). This pivoting force can cause the arm 214 to pivot about the pin 220 in a first direction (in a counterclockwise direction in the orientation of FIGS. 5-8) in the absence of countervailing forces.

In some embodiments, the force limiting mechanism 210 can comprise one or more additional pulleys around which the actuation member 208 is routed within the handle 202. In other embodiments, the force limiting mechanism 210 can comprise a single pulley around which the actuation member 208 is routed. For example, in a specific implementation, the second pulley 234 can be eliminated and the proximal end portion 208p of the actuation member can extend toward a control mechanism on or adjacent to the second side 240 of the handle.

In alternative embodiments, the actuation member 208 can be routed around and slide relative to adjacent surfaces of the arm 214 and/or the handle 202 rather than one or both pulleys 228, 234. For example, in a specific implementation, in place of pulleys 228, 234, the actuation member 208 can be routed around curved surfaces on the arm 214 and the inside of the handle 202.

In the illustrated embodiment, the force limiting mechanism 210 can further comprise a biasing member, such as a coil spring 242, configured to bias the pivoting arm 214 to a release position (the downward position shown in FIG. 6; discussed further below). A first end portion of the spring 242 can be coupled to a spring base 244, which is connected to the first side 226 of the handle 202. In particular embodiments, the first end portion of the spring 242 can comprise a first spring hook 245 that can be hooked onto a bar or pin (not shown) of the spring base 244 to connect the spring 242 to the spring base 244. A second end portion of the spring 242 can be coupled to the second end portion 232 of the arm 214. In particular embodiments, the second end portion of the spring 242 can comprise a hook 246, as shown in FIG. 6. The arm 214 can comprise a projection 248 that can extend from the second end portion 232 of the arm. The projection 248 can be connected to the arm 214 by a pin 250. In particular embodiments, the hook 246 can extend around the projection 248, thereby coupling the hook to the arm.

The spring 242 can be an extension spring such that it remains in a contracted state, as shown in FIG. 6, when no force is applied to it, and linearly expands to an expanded state, as shown in FIG. 7, when a linear expansion force greater than a threshold amount is applied to it. Thus, the spring 242 can exert a biasing force on the second end portion 232 of the arm 214. This biasing force can be selected to limit the amount of force that can be applied by the actuation member 208 to the prosthetic valve 100, as explained below. In alternative embodiments, other types of springs and other types of biasing members can be used in lieu of the coil spring 242, including, without limitation, a torsion spring, an elastic band, or other biasing means. When a torsion spring is utilized, it can be situated adjacent the pivot element 220 of the arm 214 and can have opposing end portions that bear against the arm 214 and the base portion 216.

When the actuation member 208 is pulled in a proximal direction with a force less than a predetermined threshold, a pivoting force is applied to the second end portion 232 of the arm 214, as explained above. This, in turn, causes a linear expansion force to be applied to the spring 242. However, the biasing force of the spring 242 can be selected such that when the force applied to the actuation member 208 is less than the threshold, the spring 242 remains in its contracted state, thereby preventing the arm 214 from pivoting and keeping the arm 214 in a first, release position as shown in FIG. 6. In the release position, the actuation member 208 can move axially between the arm 214 and the base portion 216, thereby applying a proximally directed force to the distal end portion 104 of the frame 102 and causing the frame to radially expand.

Figure 8:
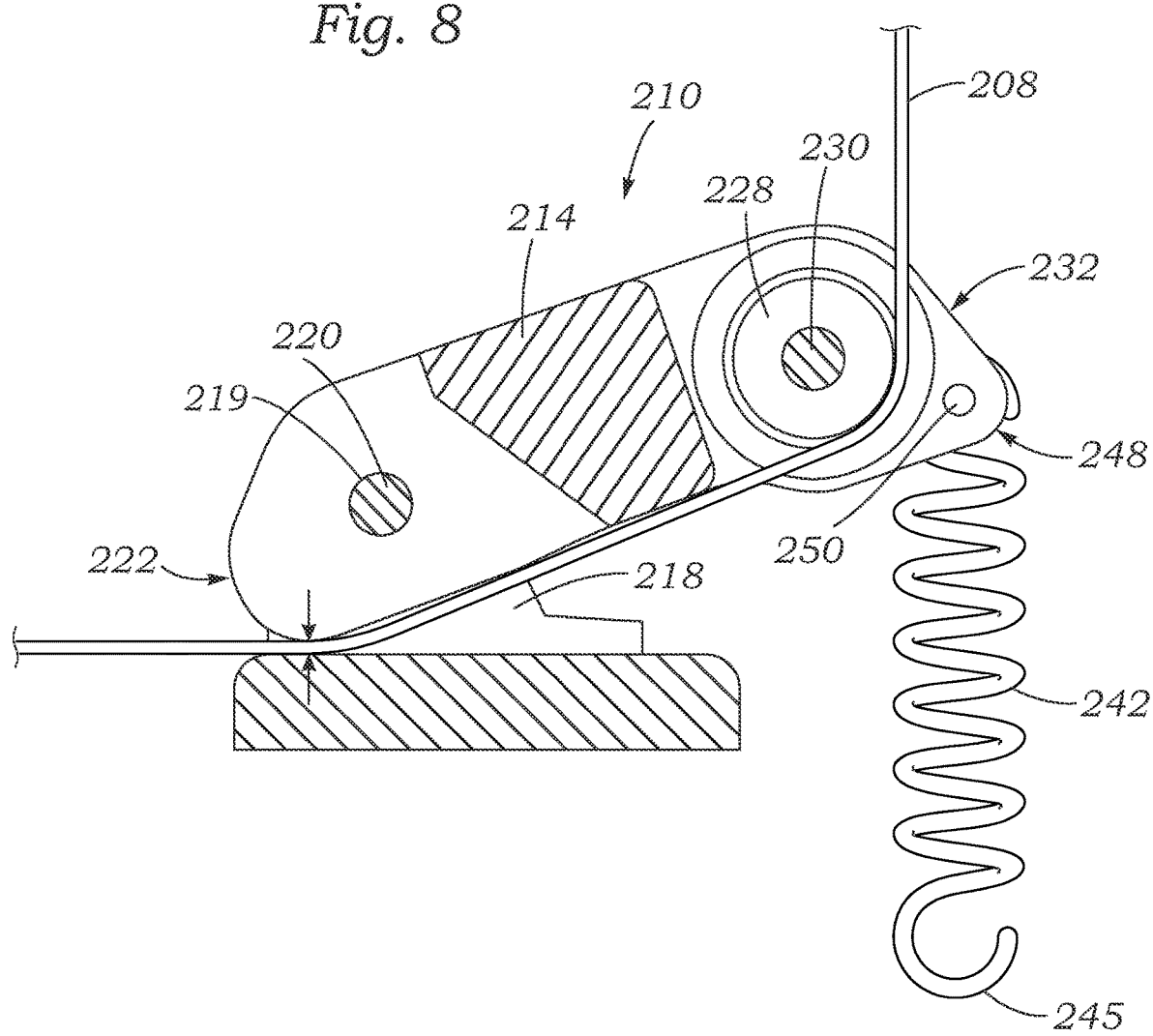
FIG. 8 is another side view of the exemplary force limiting mechanism of FIG. 6, shown partially in cross-section.

When the actuation member 208 is pulled in a proximal direction with a force greater than the predetermined threshold, a greater upwardly directed force is applied to the second end portion 232 of the arm 214, thereby causing a greater linear expansion force to be applied to the spring 242. The biasing force of the spring 242 can be selected such that when the force applied to the actuation member 208 is greater than the predetermined threshold, the spring 242 expands to its expanded state. This allows the arm 214 to pivot to a second, engaged position, in which the actuation member 208 is pinched between the first end portion 222 of the arm 214 and an adjacent surface of the base portion 216, as shown in FIGS. 7-8. The force applied to the actuation member 208 by the first end portion 222 of the arm 214 prevents the actuation member from moving axially between the arm 214 and the base portion 216, and thus prevents the frame 102 from further expansion.

Once the spring 242 expands and the actuation member 208 is pinched between the arm 214 and the base portion 216, additional proximally directed force applied to the actuation member 208 will create additional tension in the actuation member and will cause the arm 214 to pinch the actuation member tighter. This will increase the force preventing the actuation member 208 from axial movement between the arm 214 and the base portion 216. When the tension in the actuation member 208 is released, the spring 242 can return to its compressed state. This causes the spring 242 to pull downwards on the second end portion 232 of the arm 214, which causes the arm to pivot clockwise (in the orientation of FIGS. 5-8) and return to the first, release position, as shown in FIG. 6. In this position, the actuation member 208 is once again free to move in a proximal direction between the arm 214 and the base portion 216 to expand the prosthetic valve 100. Thus, the force limiting mechanism 210 prevents excessive forces from being transferred along the length of the delivery apparatus 200 and to the prosthetic valve 100, which can otherwise damage the delivery apparatus and/or cause trauma to the patient. Additionally, by limiting the amount of force that can be applied to the actuation member 208, the force limiting mechanism 210 assists the user in applying a constant force at a desired rate to the actuation member 208 so as to expand the prosthetic valve 100 at a desired expansion rate.

In alternative embodiments, a biasing member can be coupled between the second end portion 232 of the arm 214 and the second side 240 of the handle 202. For example, the biasing member can be a coil compression spring having one end that bears against an adjacent inner surface of the second side 240 of the handle 202 and another end that bears against an adjacent surface of the second end portion 232 of the arm 214. The compression spring can apply a biasing force against the arm 214 that biases the arm toward the release position (FIG. 6) and can become axially compressed when pivoted to the engaged position (FIG. 5) by exerting a pulling force on the actuation member 208 that exceeds the predetermined threshold.

Figure 9:
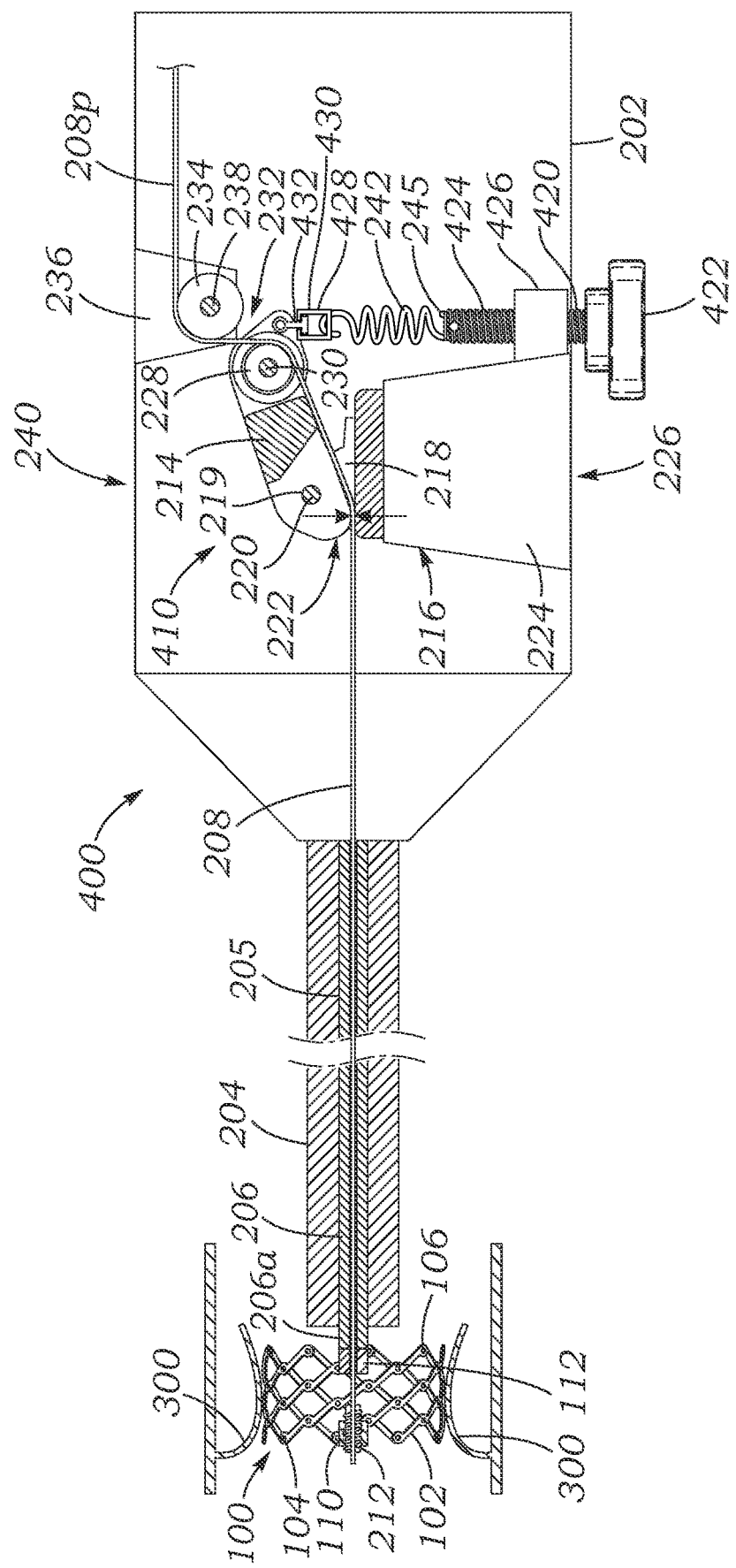
FIG. 9 is another exemplary prosthetic valve delivery apparatus shown being used to implant the prosthetic heart valve of FIG. 2.

FIG. 9 shows an exemplary embodiment of a delivery apparatus 400 comprising a force limiting mechanism 410. The force limiting mechanism 410 allows a physician to adjust the maximum amount of force that can be applied to a radially expandable prosthetic device, as described below. Many of the elements of delivery apparatus 400 are the same as the elements of the delivery apparatus 200 and many of the elements of the force limiting mechanism 410 are the same as the elements of force limiting mechanism 210. Accordingly, the same reference numbers used to describe the elements of the delivery apparatus 200 and the force limiting mechanism 210 are used to describe elements that are also present in the delivery apparatus 400 and the force limiting mechanism 410.

The force limiting mechanism 410 comprises the same elements as the force limiting mechanism 210 except that the force limiting mechanism 410 does not comprise a spring base 244 and instead comprises an adjustment member or mechanism, such as an adjustment screw 420, configured to adjust the bias of the spring 242 as explained below. Adjusting the bias of the spring 242 can increase or decrease the maximum amount of force (also referred to herein as a predetermined threshold force) that can be applied to the prosthetic valve as described below. This can allow a physician to adjust the maximum radial force that can be applied by the prosthetic valve against the native annulus for each patient individually, which can be beneficial for patients that have a higher risk of annular rupture than others (e.g., based on calcification level, calcification distribution, calcification geometry, whether a bicuspid valve is present, and/or other factors).

In particular embodiments, the adjustment screw 420 can comprise a screw head 422 and a threaded portion 424. The screw head 422 can be positioned outside of the handle 202 and the threaded portion 424 can extend through an opening in the first side 226 of the handle and an internally threaded portion 426 adjacent the first side 226 of the handle. The threaded portion 426 can have an internally threaded surface that can engage the threaded portion 424 of the screw 420. This can allow the adjustment screw 420 to be screwed into or out of the first side 226 of the handle 202. The screw head 422 can have a textured outer surface, such as ridges, to aid a user in grasping and rotating it. The internally threaded portion 426 can be a nut that can be secured to an inner surface of the first side 226 of the handle.

A first end portion of the threaded portion 424 of the screw 420 can be coupled to the first spring hook 245 at the first end portion of the spring 242. In particular embodiments, the end portion of the threaded portion 424 adjacent the screw can have an opening through which the first spring hook 245 can extend. In other embodiments, the first spring hook 245 can be welded or otherwise coupled or connected to the threaded portion 424 of the adjustment screw 420 using other techniques and/or mechanisms.

The second end portion of the spring 242 can be coupled to the pivot arm 214 by a swivel joint 428 configured to permit rotation of the spring relative to the pivot arm 214. The swivel joint 428 comprises a female component configured as a socket 430 and a male component configured as a pin or shaft 432 having an enlarged end portion that is captured within the socket 430. The second end portion of the spring 242 (which can be in the shape of a hook, as shown) can be connected to the socket 430 (for example, the hook of the spring can extend through one or more openings in the socket). An upper portion of the shaft 432 can be connected to the second end portion 232 of the pivot arm 214 (e.g., the shaft 432 can be connected to the pin 250). The interior of the socket 430 is sized to permit relative rotation between the socket 430 and the shaft 432. This allows the screw 420 and the spring 242 to freely rotate relative to the pivot arm 214 upon adjustment of the screw, as described further below. In other embodiments, the lower end portion of the spring 242 can be coupled to the screw 420 via a respective swivel joint, or the upper and lower ends of the spring can be coupled to the pivot arm and the screw via respective swivel joints.

In particular embodiments, the screw head 422 can be rotated to screw the adjustment screw 420 further into or out of the handle 202. This can cause the first hook 245 and the first end portion of the spring 242 to move closer to or further away from the arm 214, thereby pre-compressing or pre-expanding the spring, which in turn adjusts the amount of force required to actuate the pivot arm 214 and arrest further expansion of the prosthetic valve.

Rotating the screw 420 in a first direction to move the screw further out of the handle pre-expands the spring 242 (e.g., from the relaxed state shown in FIG. 6), which will then require the user to apply a greater force to the actuation member 208 to actuate the pivot arm 214. The degree to which the adjustment screw is rotated influences the required pull force on the actuation member 208 to actuate the pivot arm. Specifically, a higher degree of rotation applied to the screw in the first direction produces a greater amount of pre-extension of the spring 242, which in turn will require the user to apply a higher pull force on the actuation member 208 relative to a non-extended state of the spring. This, in turn, will enable the actuation member 208 to be pulled to a greater extent prior to being pinched to a full stop, thereby expanding the prosthetic valve to a larger outer diameter. In other words, adjusting the screw in this manner increases the maximum force that can be applied to the prosthetic valve via the actuation member 208.

Conversely, when the adjustment screw 420 is rotated in a second direction, opposite the first direction, the screw moves into the handle 202 toward the pivot arm 214. If starting from a pre-expanded state of the spring, rotating the screw 420 in the second direction allows the spring to move toward a more relaxed state or the fully relaxed state shown in FIG. 6, which in turn decreases the amount of force required to expand the spring 242 and move the pivot arm 214 to the engaged position. In other words, adjusting the screw in this manner decreases the maximum force that can be applied to the prosthetic valve via the actuation member 208. Accordingly, the adjustment screw 420 can be used to adjust the threshold force needed to cause the spring 242 to expand and consequently, the maximum amount of force that can be applied to the prosthetic valve 100 by the actuation member 208.

In certain embodiments, further rotation of the adjustment screw 422 in the second direction when spring 242 is fully relaxed can cause the pivot arm 214 to pivot toward the engaged position (counterclockwise in the drawings) (the second end portion 232 of the pivot arm 214 moves closer to the first side 226 of the handle 202 and the first end portion 222 of the pivot arm moves closer to the base portion 216). Thus, adjustment of the screw 422 in this manner positions the pivot arm at an intermediate position between the position shown in FIG. 6 and the position shown in FIG. 7. The decreases the arc length through which the pivot arm pivots before pinching the actuation member 208. As a result, this decreases the amount of spring expansion that occurs due to pivoting motion of the pivot arm, thereby decreasing the amount of force applied by the user to arrest further motion of the actuation member 208.

In this way, adjusting the adjustment screw 422, or a similar adjustment mechanism, as described above, can adjust a predetermined threshold force exerted by the actuation member, thereby adjusting a maximum amount of force that can be applied to the prosthetic heart valve (or alternative implantable medical device). As explained herein, this adjusting can occur during an implantation procedure, during applying the proximally directed force to the prosthetic heart valve via the actuation member. In some embodiments, adjusting the predetermined force can include actuating the adjustment screw 420 to pre-expand the biasing member (e.g., spring 242) to increase a biasing force applied to the second end portion 232 of the pivot arm 214 and increase the predetermined threshold. In some embodiments, adjusting the predetermined threshold includes actuating the adjustment screw 420 to move the biasing member into a more relaxed or fully relaxed state to decrease the biasing force and decrease the predetermined threshold.

In some embodiments, the adjustment screw 420 can be rotated continuously. In other embodiments, the screw 420 can be configured to be rotated in discreet steps. For example, in some embodiments, stop members can be provided for regulating the rotation of the screw 420. Stop members can be, for example, moveable or removable pins or equivalent structures positioned to the handle to block rotation of the screw head 422 after a pre-determined amount of rotation. After the screw head comes into contact with a pin, the user can remove the pin or move it out of engagement with the screw head to permit further rotation of the screw.

In some embodiments, the screw head 422 and/or a portion of the handle can include markings indicating predetermined positions of the screw head that correspond to different force limits for the force limiting mechanism 410, such as "low" (indicating a relatively low force is required to actuate the pivot arm), "medium" (indicating a medium or intermediate force is required to actuate the pivot arm), and "high" (indicating a relatively high force is required to actuate the pivot arm).

In certain embodiments, the adjustment screw 420 can be adjusted manually by a doctor or other operator of the delivery apparatus 400. In other embodiments, the adjustment screw 420 can be adjusted automatically by a motor (e.g., an electric motor) or other mechanism that is configured to adjust the position of the adjustment screw. For example, the delivery apparatus 400 can include a controller having a user interface. The controller can be integrated into the handle 202 or it can be a separate component from the handle that is in communication with the motor (which can be in the handle) via a wired or wireless connection. The user interface can have one or more buttons (physical buttons or icons on a touch screen) that allow the user to select the force limit of the force limiting mechanism 410. Depending on the user input, the controller controls the motor to adjust the position of the adjustment screw 420 to either decrease or increase the bias of the spring 242 until the desired maximum force that can be applied to the prosthetic valve is achieved. In embodiments that include a motor to adjust the adjustment screw, the screw head 422 optionally can be eliminated or it can be disposed inside of the handle.

In alternative embodiments, the force limiting mechanism 410 can comprise other mechanical and/or electrical mechanisms configured to pre-expand or pre-compress the spring 242, thereby adjusting the maximum amount of force that can be applied to the prosthetic valve 100. Such other mechanisms can comprise, for example, ratcheting mechanisms, rack-and-pinion mechanisms, a slidable piston, electrically operable displacement mechanisms, and the like, which can be operatively connected to the spring 242 in such a manner to adjust the tension in the spring 242.

In alternative embodiments, in lieu of or in addition to the screw 422, another adjustment member can be connected to the second end portion 232 of the pivot arm 214 and can be configured to adjust the position of the pivot arm prior to expansion of the prosthetic valve. The adjustment member can be, for example, a string, tether, cable, rod, or a second spring, connected at one end to the second end portion 232 of the pivot arm 214 and extending toward the second side 240 of the handle 202. The end of the another adjustment member opposite the pivot arm 214 can be connected to a knob or equivalent mechanism on the handle that is configured to tension or pull the adjustment member toward the second side 240 of the handle. In use, prior to expanding the prosthetic valve, the adjustment member can be adjusted (e.g., by tensioning or pulling it toward the second side 240 of the handle) which causes the second end portion 232 of the pivot arm to pivot towards the second side 240 of the handle, thereby bringing the pivot arm closer to the engaged position (e.g., the pivot arm is between the position shown in FIG. 6 and the position shown in FIG. 7). As a result, when a force is applied to the actuation member 208 to expand the prosthetic valve, the pivot arm 214 can pivot to the engaged position and arrest further expansion more quickly than if the pivot arm is closer to the position shown in FIG. 6.

In still alternative embodiments, the gap between the first end portion 222 of the pivot arm 214 and the upper surface of the base portion 216, through which the actuation member 208 can pass, can be adjustable. Adjusting this gap can adjust the path of travel of the pivot arm between the release position and the engaged position. Reducing the gap can decrease the path of travel of the pivot arm 214, thereby allowing the pivot arm to reach the engaged position under lower force. Conversely, increasing the gap can increase the path of travel of the pivot arm, and the force required for the pivot arm to reach the engaged position.

Figure 11:
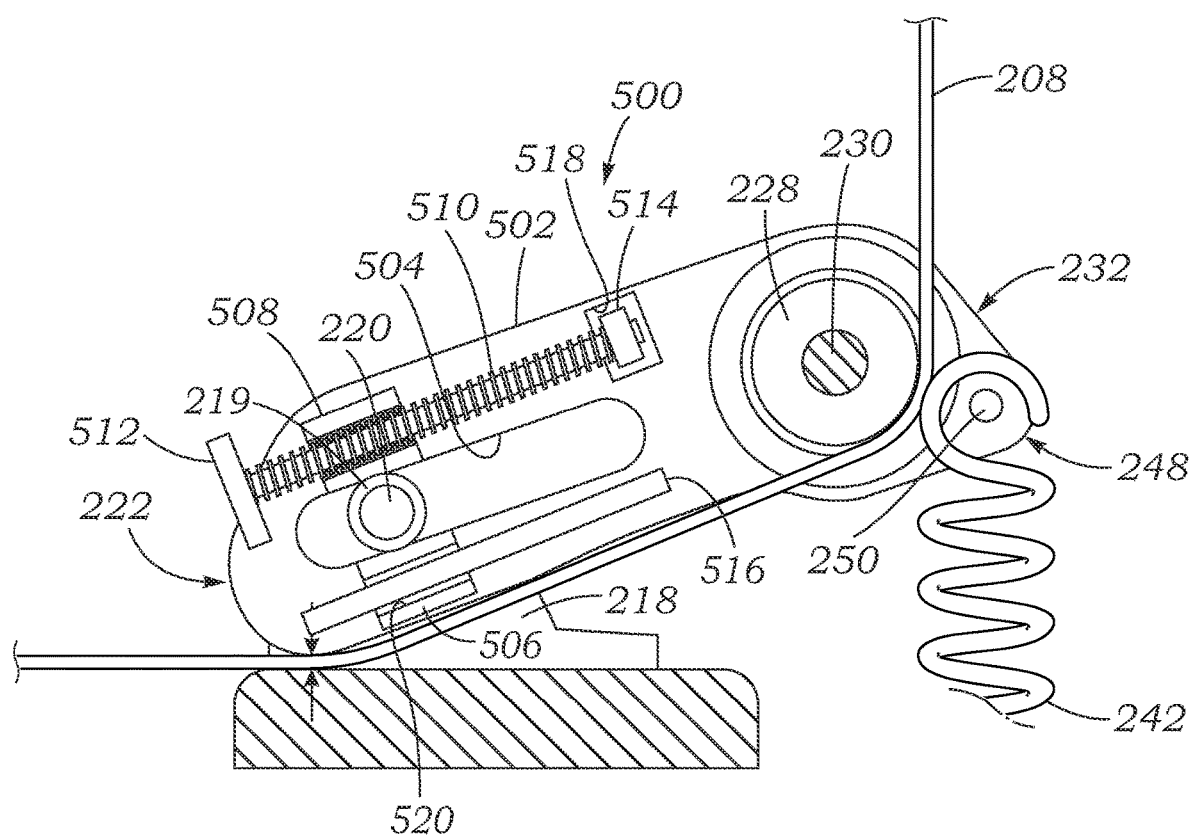
FIG. 11 is a side view of another exemplary force limiting mechanism.

FIG. 11 shows an exemplary embodiment of a force limiting mechanism 500 that has an adjustable hinge pin. Many of the elements of the force limiting mechanism 500 are the same as the elements of the force limiting mechanism 210. Accordingly, the same reference numbers used to describe the elements of the force limiting mechanism 210 are used to describe elements that are also present in the force limiting mechanism 500.

The force limiting mechanism 500 can comprise a pivot arm 502. The pivot arm 502 is similar to the pivot arm 214 except for the differences described herein. The pivot arm 500 can have a slot 504 in which the pivot element 220 can slide. The ends of the pivot element 220 can be supported in respective elongated slots (not shown) in the ears 215 of the base portion 216. By moving the pivot element 220 along the length of the slot 504, the pivot point of the arm 500 can be adjusted, thereby adjusting the arc length through which the arm pivots in order to pinch the actuation member 208. This can change the amount of spring expansion that occurs before the pivot arm pinches the actuation member 208.

The arm 500 can further comprise a sliding element 506 that can slide along a length of the pivot arm relative to the slot 504. The sliding element 506 can comprise a nut or threaded opening 508. A screw 510 can extend through the nut 508 along an upper portion of the arm 502. The screw 510 can have external threads that engage internal threads of the threaded opening 508.

A first end of the screw 510 can comprise a knob 512 that extends out of the first end portion 222 of the arm 502. A second end of the screw 510 can comprise an enlarged screw head 514 captured within an opening 518 in the pivot arm that axially retains the screw 510 relative to the arm 502. The arm 502 can also comprise a rail 516 that can extend along a lower portion of the arm 502 and through a respective opening 520 in the sliding element 208 such that the sliding element 506 can slide along the rail 516. The pivot element 220 can be coupled to the sliding element 506 such that they move together relative to the slot 504 and the rail 516. Thus, rotation of the knob 512 causes the sliding element 506 to move axially along the screw 510 and the pivot element 220 within the slot 504.

Rotation of the knob 512 in a first direction causes the pivot element 220 to move closer to the second end portion 232 of the pivot arm, which decreases the arc length through which the pivot arm pivots before pinching the actuation member 208. This decreases the amount of spring expansion that occurs due to pivoting motion of the pivot arm, thereby decreasing the amount of force applied by the user to arrest further motion of the actuation member 208. Conversely, rotation of the knob in a second direction, opposite the first direction, causes the pivot element to move closer to the first end portion 222 of the pivot arm, which increases the arc length through which the pivot arm pivots before pinching the actuation member 208. This increases the amount of spring expansion that occurs due to pivoting motion of the pivot arm, thereby increasing the amount of force applied by the user to arrest further motion of the actuation member 208.

A representative method of implanting the prosthetic heart valve 100 using the delivery apparatus 200 can proceed in the following manner. The prosthetic valve 100 can be connected to delivery apparatus 200 as described above and compressed to a radially compressed state, and optionally placed in a sheath of the delivery apparatus (e.g., the distal end portion of the shaft 204). The distal end portion of the delivery apparatus 200 (along with the prosthetic valve 100) can be advanced through a femoral artery and the aorta toward the native aortic valve 300, as shown in FIG. 5.

Once the prosthetic valve 100 is at the desired implantation location, the prosthetic valve can be deployed by, for example, rotating a knob of the handle 202 to advance the prosthetic valve 100 from the sheath. To expand the prosthetic valve 100, the inner shaft 206 can, for example, be advanced distally relative to the handle 202 or can be held against the stopper 112 while the actuation member 208 is pulled in a proximal direction. If too great a force is applied to the actuation member 208, the force limiting mechanism 210 will prevent the actuation member from being pulled further, as described above. If this occurs, the user can release or decrease the pulling force applied to the actuation member 208, allowing the force limiting mechanism 210 to release the actuation member. Additional expansion of the prosthetic valve 100 can then be achieved by again pulling the actuation member 208 in a proximal direction.

Figure 10:
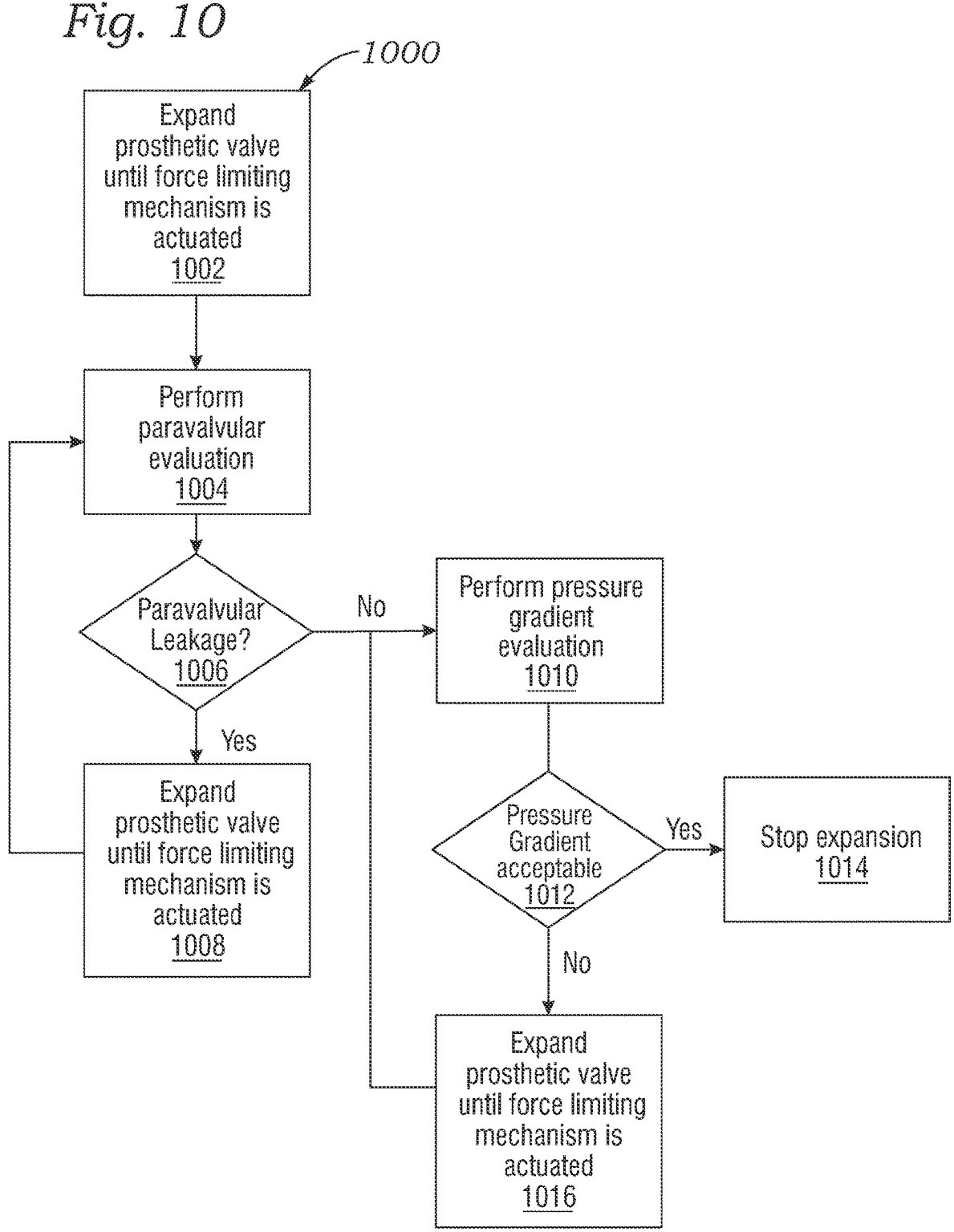
FIG. 10 shows a flow chart of an exemplary method for implanting the prosthetic heart valve of FIG. 2.

FIG. 10 shows a flow chart 1000 of another representative method for expanding the prosthetic heart valve using the delivery apparatus 400. The delivery apparatus 400 can be used to expand the prosthetic valve 100 until the diameter of the native anatomy is reached (block 1002). Prior to valve expansion, the adjustment screw 420 can be pre-set to a value whereby the force limiting mechanism 410 prevents further expansion of the prosthetic valve 100 once the prosthetic valve comes into contact with the native annulus. For example, prior to valve expansion, the adjustment screw 420 can be used to set the force limiting mechanism 410 based on the patient's anatomy (e.g., calcification level, bi-cuspid valve, etc.). For patients with a high risk of annular rupture, the screw 420 can be used to set the force limitation mechanism 410 to a low force level. For patients with a relatively lower risk of annular rupture, the screw 420 can be used to set the force limitation mechanism 410 to a higher force level.

In some cases, the physician can use the delivery apparatus to rapidly expand the prosthetic valve 100 until the force limiting mechanism 410 prevents further expansion. In other cases, the physician can expand the prosthetic valve at a relatively slower pace and monitor the hemodynamics of the prosthetic valve (e.g., paravalvular leakage and pressure gradient) and if the physician determines that the hemodynamics are satisfactory, the physician can cease further expansion before the force limiting mechanism 410 is ever actuated. Thus, in such cases, the physician may be able to complete the implantation process without the force limiting mechanism being actuated.

If the force limiting mechanism is actuated, a paravalvular leak evaluation can then be performed (block 1004), such as using echocardiography (e.g., transesophageal echocardiography or transaortic echocardiography). If there is any paravalvular leakage, the adjustment screw 420 can be adjusted to increase the maximum force that can be applied and the prosthetic valve 100 can be further expanded slowly until expansion is arrested by the force limiting mechanism (block 1008). The user can then re-assess for paravalvular leaks (block 1004) and if necessary, further adjust the adjustment screw and further expand the prosthetic valve. The process of checking for paravalvular leaks and further expanding the prosthetic valve can be repeated incrementally as desired until the proper sealing of the prosthetic valve with the native anatomy is achieved.

If there is no paravalvular leakage, a pressure gradient evaluation can be performed (for example, by using echocardiography) (block 1010). If the pressure gradient is acceptable (e.g., 2-3 mmHG or less), then expansion of the prosthetic valve 100 can be stopped (block 1014) and the delivery apparatus can be released from the prosthetic valve and removed from the patient. If the pressure gradient needs to be decreased (e.g., it is 3 mmHg or higher), the adjustment screw 420 can be adjusted to increase the maximum force that can be applied and the prosthetic valve 100 can continue to be expanded slowly (block 1016). Expansion of the prosthetic valve 100 can continue until either the pre-set maximum force limit is met. The user can then re-assess the pressure gradient and if necessary, further adjust the adjustment screw and further expand the prosthetic valve. The process of assessing the pressure gradient and further expanding the prosthetic valve can be repeated incrementally as desired until the desired pressure gradient is achieved.

Although the disclosed embodiments pertain generally to delivery apparatuses and methods for implantation of prosthetic heart valves in the native aortic valve, it should be understood that the disclosed embodiments can be used to implant prosthetic devices at any location of the heart or elsewhere in the body. Additionally, although the disclosed embodiments pertain generally to transfemoral delivery of prosthetic devices, it should be understood that the disclosed embodiments can be adapted for use with, for example, transapical procedures, transaortic procedures, trans-subclavian procedures, transradial procedures, or trans-septal procedures.

Additionally, the force limiting mechanism 210 can be incorporated in various other types of delivery apparatuses to control the amount of force that can be applied to an actuation member. For example, known delivery apparatuses for self-expandable prosthetic valves typically have one or more actuation members in the form of sutures that extend around or through portions the prosthetic valve. The sutures (also referred to as tension members) are coupled to the prosthetic valve such that decreasing tension applied to the sutures allows the prosthetic valve or a portion thereof to self-expand to an expanded state, while increasing tension applied to the sutures radially compresses the prosthetic valve or a portion thereof to a compressed state. The sutures therefore can be used to control expansion of the prosthetic valve. One such example of a self-expandable prosthetic valve and a delivery apparatus that uses sutures to control expansion of the prosthetic valve is disclosed in U.S. Pat. No. 7,837,727, which is incorporated herein by reference. In particular embodiments, a delivery apparatus for a self-expandable prosthetic valve can include at least one actuation member (e.g., a suture) that controls expansion of the prosthetic valve and a force limiting mechanism 210 configured to limit the amount of force that can be applied to the actuation member when radially compressing the prosthetic valve.

The force limiting mechanism 210 also can be incorporated into various other types of medical devices to control the amount of force that can be applied to an actuation member.

General Considerations

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

All features described herein are independent of one another and, except where structurally impossible, can be used in combination with any other feature described herein. For example, a delivery apparatus 200 as shown in FIG. 5 can be used in combination with prosthetic valve 10. In another embodiment, a locking mechanism as shown in FIG. 1 can be used in combination with the prosthetic valve 100 shown in FIG. 2.

As used in this application and in the claims, the singular forms "a," "an," and "the" include the plural forms unless the context clearly dictates otherwise. Additionally, the term "includes" means "comprises." Further, the term "coupled" generally means physically, mechanically, chemically, magnetically, and/or electrically coupled or linked and does not exclude the presence of intermediate elements between the coupled or associated items absent specific contrary language.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device away from the implantation site and toward the user (e.g., out of the patient's body), while distal motion of the device is motion of the device away from the user and toward the implantation site (e.g., into the patient's body). The terms "longitudinal" and "axial" refer to an axis extending in the proximal and distal directions, unless otherwise expressly defined.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope of these claims.

We claim:

1. A medical assembly comprising:
   a prosthetic heart valve that is radially expandable and compressible between a radially compressed configuration and a radially expanded configuration; and
   a delivery apparatus comprising:
      a handle;
      at least one actuation member extending from the handle and coupled to the prosthetic heart valve, wherein the at least one actuation member is configured to apply a proximally directed force to the prosthetic heart valve to cause the prosthetic heart valve to foreshorten axially and expand radially; and
      a force limiting mechanism positioned within the handle and comprising a pivot arm and a base portion, wherein the pivot arm is pivotably coupled to the base portion, wherein the actuation member is movably coupled to the pivot arm such that a force applied to the actuation member causes the pivot arm to pivot relative to the base portion;
      wherein the force limiting mechanism is configured to pinch the at least one actuation member between the pivot arm and the base portion when the force applied to the at least one actuation member exceeds a predetermined force, thereby preventing proximal movement of the at least one actuation member, and wherein the force limiting mechanism permits proximal movement of the at least one actuation member to produce radial expansion of the prosthetic heart valve when the force applied to the at least one actuation member is less than the predetermined force.

2. The medical assembly of claim 1, wherein the at least one actuation member extends around a pulley mounted on the pivot arm, wherein the pulley can pivot with the pivot arm upon application of the force to the at least one actuation member, and wherein the at least one actuation member extends between the pivot arm and the base portion.

3. The medical assembly of claim 2, wherein the pulley comprises a first pulley and the at least one actuation member further extends around a second pulley coupled to the handle and spaced from the pivot arm, the second pulley positioned proximal to the pivot arm, and wherein the base portion is connected to a first side of the handle and the second pulley is connected to a second side of the handle, the second side opposite the first side.

4. The medical assembly of claim 1, wherein the force limiting mechanism further comprises a biasing member configured to exert a biasing force against the pivot arm, wherein the biasing force is selected such that:
when the force applied to the at least one actuation member is less than the predetermined force, the pivot arm is prevented from pivoting relative to the base portion, against the biasing force; and
when the force applied to the at least one actuation member exceeds the predetermined force, the pivot arm pivots relative to the base portion.

5. The medical assembly of claim 4, wherein the biasing member comprises a spring that is linearly expandable between a compressed configuration and an expanded configuration, wherein one end portion of the spring is coupled to the pivot arm, wherein another end portion of the spring is coupled to the handle, and wherein the spring is configured such that a proximally directed force applied to the at least one actuation member causes an expansion force to be applied to the spring.

6. The medical assembly of claim 4, further comprising an adjustment mechanism configured to adjust the predetermined force, and wherein the adjustment mechanism comprises an adjustment screw comprising a threaded portion that extends through the handle and is coupled to the biasing member.

7. The medical assembly of claim 6, wherein the adjustment screw further comprises a screw head coupled to the threaded portion, the screw head arranged outside of the handle, wherein the handle includes an internally threaded portion secured to an internal surface of the handle, the internally threaded portion having an internally threaded surface configured to engage with the threaded portion of the adjustment screw, wherein the adjustment screw is rotatable in a first direction which moves the adjustment screw further outside of the handle, pre-expands the biasing member, and increases the predetermined force, and wherein the adjustment screw is rotatable in a second direction, opposite the first direction, which moves the adjustment screw into the handle and toward the pivot arm, moves the biasing member to a more relaxed state or a fully relaxed state, and decreases the predetermined force.

8. The medical assembly of claim 4, wherein the pivot arm is pivotably coupled to the base portion by a pivot element extending through a first end portion of the pivot arm and the base portion, further comprising an adjustment mechanism configured to adjust the predetermined force, and wherein the adjustment mechanism comprises a sliding element arranged within the pivot arm and coupled to the pivot element, the pivot element arranged within an elongate slot extending from the first end portion of the pivot arm, toward a second end portion of the pivot arm, the pivot element configured to slide along the slot in response to movement of the sliding element within the pivot arm, where a position of the pivot element determines a pivot point of the pivot arm and an arc length through which the pivot arm pivots in order to pinch the actuation member.

9. The medical assembly of claim 1, wherein the actuation member is one of a flexible cable, a suture, a wire, a cord, a flexible rod, and a flexible shaft.

10. A delivery apparatus for an implantable medical device comprising
a handle;
at least one actuation member extending from the handle and coupled to the medical device, wherein the at least one actuation member is configured to apply a proximally directed force to the medical device; and
a force limiting mechanism arranged within the handle, the force liming mechanism comprising a pivot arm configured to limit an amount of the proximally directed force that can be applied by the at least one actuation member to the medical device.

11. The delivery apparatus of claim 10, wherein the pivot arm is configured to prevent the at least one actuation member from applying a proximally directed force to the medical device if a proximally directed force greater than a predetermined threshold is applied to the at least one actuation member, wherein the force limiting mechanism further comprises a base portion, and wherein the pivot arm is configured to pivot and retain the at least one actuation member between the pivot arm and the base portion if a proximally directed force greater than the predetermined threshold is applied to the at least one actuation member.

12. The delivery apparatus of claim 11, wherein the force limiting mechanism further comprises a biasing member configured to exert a biasing force against the pivot arm and prevent pivoting of the pivot arm if the proximally directed force applied to the at least one actuation member is less than the predetermined threshold and permit pivoting of the pivot arm if the proximally directed force applied to the at least one actuation member exceeds the predetermined threshold.

13. The delivery apparatus of claim 12, wherein the biasing member comprises a spring.

14. The delivery apparatus of claim 12, wherein the force limiting mechanism further comprises an adjustment screw including a threaded portion in threaded engagement with an internally threaded portion of the handle, where a first end of the threaded portion is coupled to the biasing member and a second end of the threaded portion is configured to be rotated in a first direction that increases the biasing force and an opposite, second direction that decreases the biasing force.

15. The delivery apparatus of claim 12, wherein the pivot arm includes an adjustable pivot element about which the pivot arm pivots relative to the base portion, and wherein the pivot element is configured to slide within an elongated slot of the pivot arm extending from a first end portion toward a second end portion of the pivot arm, in response to linear translation of a sliding element coupled to the pivot element and in sliding engagement with a portion of the pivot arm, in order to adjust a position of a pivot point of the pivot arm.

16. The delivery apparatus of claim 10, wherein the force limiting mechanism further comprises a pulley mounted on the pivot arm and the at least one actuation member is routed at least partially around the pulley.

17. The delivery apparatus of claim 10, wherein the at least one actuation member is configured to produce radial expansion of the medical device upon application of the proximally directed force to the at least one actuation member, wherein the medical device is a mechanically expandable prosthetic heart valve including a plurality of interconnected struts, and wherein the struts are pivotably coupled to one another at one or more pivot joints arranged along a length of each strut.

18. A method of implanting a prosthetic heart valve, comprising:
   inserting into a body of a patient a distal end portion of a delivery apparatus and a prosthetic heart valve coupled to the distal end portion of the delivery apparatus in a radially compressed configuration, the delivery apparatus comprising:
      a handle;
      at least one actuation member extending from the handle and coupled to the prosthetic heart valve and configured to apply a proximally directed force to the prosthetic heart valve to cause the prosthetic heart valve to foreshorten axially and expand radially; and
      a force limiting mechanism configured to limit an amount of the proximally directed force that can be applied by the at least one actuation member to the prosthetic heart valve;
   advancing the delivery apparatus distally until the prosthetic heart valve is disposed at a selected implantation site; and
   radially expanding the prosthetic heart valve by applying a proximally directed force to the at least one actuation member so as to move the at least one actuation member relative to the force limiting mechanism.

19. The method of claim 18, further comprising, when the proximally directed force applied to the at least one actuation member exceeds a predetermined force during the radially expanding the prosthetic heart valve, arresting movement of the at least one actuation member with the force limiting mechanism and stopping radially expanding the prosthetic heart valve, and wherein arresting movement of the at least one actuation member with the force limiting mechanism includes pivoting a first end portion of a pivot arm of the force limiting mechanism into engagement with the at least one actuation member and pinching the at least one actuation member between the first end portion and a base portion of the force liming mechanism to which the pivot arm is coupled.

20. The method of claim 19, further comprising, in response to the proximally directed force applied to the at least one actuation member exceeding the predetermined force, decreasing an amount of the proximally directed force applied to the at least one actuation member so that it is less than the predetermined force, and then further moving the at least one actuation member relative to the force limiting mechanism, and wherein further moving the at least one actuation member relative to the force limiting mechanism includes moving the first end portion of the pivot arm out of engagement with the at least one actuation member and allowing the at least one actuation member to slide relative to the pivot arm.

* * * * *